United States Patent
Pan

(10) Patent No.: US 10,227,387 B2
(45) Date of Patent: Mar. 12, 2019

(54) TARGETED DELIVERY OF PROTEINS ACROSS THE BLOOD-BRAIN BARRIER

(75) Inventor: Dao Pan, Cincinnati, OH (US)

(73) Assignee: Children's Hospital Medical Center, Cincinnati, OH (US)

(*) Notice: Subject to any disclaimer, the term of this patent is extended or adjusted under 35 U.S.C. 154(b) by 87 days.

(21) Appl. No.: 14/117,978

(22) PCT Filed: May 18, 2012

(86) PCT No.: PCT/US2012/038627
§ 371 (c)(1),
(2), (4) Date: Apr. 9, 2014

(87) PCT Pub. No.: WO2012/159052
PCT Pub. Date: Nov. 22, 2012

(65) Prior Publication Data
US 2014/0219974 A1    Aug. 7, 2014

Related U.S. Application Data

(60) Provisional application No. 61/519,228, filed on May 18, 2011.

(51) Int. Cl.
| | |
|---|---|
| *C07K 14/47* | (2006.01) |
| *A61K 9/19* | (2006.01) |
| *A61K 38/47* | (2006.01) |
| *A61K 9/00* | (2006.01) |
| *A61K 48/00* | (2006.01) |

(52) U.S. Cl.
CPC ............ *C07K 14/47* (2013.01); *A61K 9/0019* (2013.01); *A61K 38/47* (2013.01); *A61K 48/0075* (2013.01); *C12Y 302/01076* (2013.01); *C07K 2319/10* (2013.01); *C07K 2319/33* (2013.01); *C12N 2740/15043* (2013.01)

(58) Field of Classification Search
None
See application file for complete search history.

(56) References Cited

U.S. PATENT DOCUMENTS

| | | | |
|---|---|---|---|
| 7,220,833 B2 | 5/2007 | Nelson et al. | |
| 2002/0132769 A1* | 9/2002 | Kaleko | A61K 47/48776 424/93.21 |
| 2003/0077641 A1* | 4/2003 | Laskowitz | A61K 38/16 435/6.16 |
| 2007/0082380 A1* | 4/2007 | Pardridge | C07K 14/475 435/69.1 |
| 2010/0015117 A1* | 1/2010 | Verma et al. | 424/94.1 |
| 2010/0286025 A1 | 11/2010 | Anantharamaiah et al. | |
| 2010/0331363 A1* | 12/2010 | Lansbury, Jr. | A61K 31/4709 514/312 |
| 2010/0331676 A1* | 12/2010 | Carpenter | A61B 6/481 600/431 |
| 2011/0021413 A1 | 1/2011 | Laskowitz et al. | |
| 2016/0269659 A1* | 9/2016 | Ikeda | H04N 5/35581 |

FOREIGN PATENT DOCUMENTS

| | | |
|---|---|---|
| AU | 2002322720 B2 | 2/2003 |
| WO | 2005/002515 A2 | 1/2005 |
| WO | WO 2005/002515 | 1/2005 |
| WO | WO2009032693 * | 3/2009 |

OTHER PUBLICATIONS

Davies 2005 "FKBP52" IJBCB 37:42-47.*
Uniprot P02649 "APOE_HUMAN" accessed from uniprot.org on Aug. 21, 2015.*
Uniprot P08226 "APOE_MOUSE" accessed from uniprot.org on Aug. 21, 2015.*
Kreuter 2002 "apolipoprotein-mediated transport of nanoparticle-bound drugs across the blood-brain barrier" j drug targeting 10(4):317-325.*
BPAI 2008 "Ex parte Kenichi Miyazaki" USPTO.*
Sauer 2005 "An apolipoprotein E-derived peptide mediates uptake of sterically stabilized liposomes into brain capillary endothelial cells" Biochemistry 44:2021-2029.*
Wang 1997 "Identification of a neuronal endocytic pathway activated by an apolipoprotein E (apoE) receptor binding peptide" Brain Research 778:6-15.*
Barbosa, I. et al., Glycobiology 13:647-53 (2003).
Basford, J. et al., J. Biol. Chem. 286:13079-87 (2011).
Bu, G. Nat. Rev. Neuosci. 10:333-44 (2009).
Giaume, C. et al. Nat. Rev. Neurosci. 11:87-99 (2010).
Hui, D. et al. J. Biol. Chem. 256:5646-55 (1981).
International Search Report and Written Opinion, dated Dec. 3, 2012, 11 pages.
Kreuter, J. et al., J. Control. Release 118:54-8 (2007).
Lillis, A. et al., Physiol. Rev. 88:887-918 (2008).
Moreau-Gaudry, F. et al., Blood 98:2664-2672 (2001).
Pan, W. et al., J. Cell Sci. 117:5071-8 (2004).
Pan, D. et al., Brain Res. 1188:241-53 (2008).
Pan, D. et al., Gene Ther. 7:1875-83 (2000).
Pardridge, W. Nat. Rev. Drug Discov. 1:131-9 (2002).
Spencer, B. and Verma, I. Proc. Natl. Acad. Sci. U.S.A. 104:7594-9 (2007).

(Continued)

*Primary Examiner* — Adam Weidner
(74) *Attorney, Agent, or Firm* — ALGM LLP; Harry J Guttman

(57) ABSTRACT

Embodiments of the invention are directed to compositions comprising a peptide sequence, or a nucleic acid encoding the same, wherein the peptide sequence includes a receptor-binding region of apolipoprotein E (apoE), or a sequence variant or fragment thereof, for directing delivery of a given protein or therapeutic across the blood brain barrier. Embodiments of the invention are also directed to methods of using the compositions for treating or preventing a neurological disorder, disease, or symptom in a subject in need thereof.

7 Claims, 20 Drawing Sheets

Specification includes a Sequence Listing.

(56) References Cited

OTHER PUBLICATIONS

Ueno, M. et al., Curr. Med.Chem. 17:1125-38 (2010).
Urayama, A. et al., Proc Natl Acad Sci U.S.A. 101:12658-12663 (2004).
Wang, D. et al., Proc. Natl. Acad. Sci. U.S.A. 106:19958-63 (2009).
Wang, D. et al., J. Gene Med. 10:249-59 (2008).
Williams, S. et al., J. Biol. Chem. 267:9035-40 (1992).
EP 12786131.8, Search report dated Dec. 18, 2014, 7 pages.
PCT US2012/038627, International Preliminary Report on Patentability, dated Nov. 19, 2013, 5 pages.
PCT US2012/038627, International Search Report dated Dec. 3, 2012, 5 pages.
PCT US2012/038627, Written Opinion dated Dec. 3, 2012, 4 pages.
Dodart et al., "Gene delivery of human apolipoprotein E alters brain Ab burden in a mouse model of Alzheimer's disease" PNAS (2005) vol. 102, No. 4, pp. 1211-1216.
El-Amouri et al., "Secreted Luciferase for In Vivo Evaluation of Systemic Protein Delivery in Mice" Mol. Biotechnol. (2013) vol. 53, No. 1, pp. 63-73.
El-Amouri et al., "Normalization and Improvement of CNS Deficits in Mice with Hurler Syndrome After Long-term Peripheral Delivery of BBB-targeted Iduronidase" Mol. Therapy (2014) vol. 22, No. 12, pp. 2028-2037.
Sege et al., "Expression and regulation of human low-density lipoprotein receptors in Chinese hamster ovary cells" Nature (1984) vol. 307, pp. 742-745.
Sorrentino et al., "A highly secreted sulphamidase engineered to cross the blood-brain barrier corrects brain lesions of mice with mucopolysaccharidoses type IIIA" EMBO Mol. Med. (2013) vol. 5, pp. 675-690.
Spencer et al., "Targeted delivery of proteins across the blood-brain barrier" PNAS (2007) vol. 104, No. 18, pp. 7594-7599.
Worsham et al., "In Vivo Gene Transfer into Adult Stem Cells in Unconditioned Mice by in Situ Delivery of a Lentiviral Vector" Mol. Therapy (2006) vol. 14, No. 4, pp. 514-524.
Dyer et al., "A Synthetic Peptide Mimic of Plasma Apolipoprotein E That Binds the LDL Receptor," The Journal of Biological Chemistry, Dec. 5, 1991, pp. 22803-22806, vol. 266(34).
Miao et al., "High-Level Factor VIII Gene Expression In Vivo Achieved by Nonviral Liver-Specific Gene Therapy Vectors" (2003) Human Gene Therapy, vol. 14, pp. 1297-1305.
Pan, "Cell- and Gene-based Therapeutic Approaches for Neurological Deficits in Mucopolysaccharidoses" (2011) Current Pharmaceutical Biotechnology, vol. 12, pp. 884-896.
EP 12786131, Article 94(3) EPC Communication dated Jun. 14, 2016, 6 pages.
Lentz et al., "Viral Vectors for Gene Delivery to the Central Nervous System" Neurobiol Dis. (2012) vol. 48, No. 2, pp. 179-188.
St. George "Gene therapy progress and prospects: adenoviral vectors" Gene Therapy (2003) vol. 10, pp. 1135-1141.
EP 12786131, Article 94(3) EPC Communication dated Feb. 7, 2017, 10 pages.
EP 12786131, Article 94(3) EPC Communication dated Oct. 6, 2017, 7 pages.
EP 12786131, Article 94(3) EPC Communication dated Apr. 16, 2018, 4 pages.

* cited by examiner

B $F_{MPS}$  $F_{Normal}$ $F_{MPS}$ +IDUA  $F_{MPS}$ +IDUAe1

$F_{MPS}$+IDUAe2  $F_{MPS}$ +IDUAe5

TARGETED DELIVERY OF PROTEINS ACROSS THE BLOOD-BRAIN BARRIER

CROSS-REFERENCE TO RELATED APPLICATIONS

The present application is a U.S. National Stage entry under 35 U.S.C. § 371 of International Application No. PCT/US12/38627, filed on May 18, 2012, designating the United States of America and published in English on Nov. 22, 2012, which in turn claims priority to U.S. Provisional Application No. 61/519,228, filed on May 18, 2011, each of which is hereby incorporated by reference in its entirety.

STATEMENT REGARDING FEDERALLY-SPONSORED RESEARCH

This invention was made with government support under NS064330 awarded by National Institutes of Health. The government has certain rights in the invention.

FIELD OF THE INVENTION

The invention disclosed herein generally relates to the receptor-binding region of apolipoprotein E (apoE) and compositions and methods of using the same to deliver therapeutic proteins across the blood brain barrier.

BACKGROUND

The blood-brain barrier (BBB) is primarily formed by brain capillary endothelial cells (BCECs), which are highly specialized endothelial cells with unique morphology, biochemistry, and function. Astrocytic endfeet surround more than 90% of the BCEC abluminal surface and, together with neuronal endings that directly innervate the BCEC, influence the "tightness" and trafficking role of the barrier.

The surface area of the human brain blood microvasculature available for protein/vector/therapeutic transport is ~20 m$^2$. The microvasculature is so dense that all neuron and glial cells are within a 20 μm proximity (Giaume, C. et al. Nat. Rev. Neurosci. 11:87-99 (2010)); therefore, a protein/vector/therapeutic can potentially reach the entire brain volume. If a substance can be delivered across the BBB or bypass this barrier, systemic delivery via circulation can provide an ideal noninvasive method for rapid and wide distribution of neurotherapeutics throughout the brain.

However, the barrier properties of the BBB formed by the BCECs restrict delivery of almost all neurotherapeutic agents from the blood circulation to the brain. Only small and lipophilic molecules (<0.5 kD) or those that bind to one of the receptors on BCEC can be transported effectively across the BBB (Pardridge, W. Nat. Rev. Drug Discov. 1:131-9 (2002)).

SUMMARY OF THE INVENTION

Embodiments of the invention are directed to compositions including a peptide sequence, the peptide sequence containing a receptor-binding region of apolipoprotein E (apoE), or a sequence variant, fragment, or oligomer thereof, and a protein to be delivered across the blood-brain barrier (BBB), wherein the peptide sequence containing a receptor-binding region and the protein are expressed as a fusion protein.

Embodiments of the invention are also directed to compositions that include a nucleic acid molecule, wherein the nucleic acid molecule contains a sequence encoding a fusion protein, the fusion protein including a peptide sequence containing a receptor-binding region of apoE, or a sequence variant, fragment, or oligomer thereof, and a protein to be delivered across the BBB. In some embodiments, the sequence encoding the fusion protein can be operably linked to a tissue-specific or cell-specific promoter.

Embodiments of the invention are also directed to methods of delivering a protein to the central nervous system (CNS) of a subject, the methods including administering to a subject a peptide sequence that contains the protein to be delivered fused to peptide sequence containing a receptor-binding region of apoE, or a sequence variant, fragment, or oligomer thereof, wherein administration of the peptide sequence results in delivery of the protein to the CNS. In some embodiments, these methods can be used to treat or prevent a neurological disorder, disease, or symptom in a subject in need thereof. In some embodiments, administration includes one or more of intravenous, intramuscular, oral, sublingual, buccal, parenteral, subcutaneous, intra-arterial, intraperitoneal, intracisternal, intravesical, intrathecal, transdermal, bone marrow transplantation, or rectal delivery methods. In some embodiments, the administration of the fusion protein can be via enzyme replacement therapy. In some embodiments, the fusion protein can be generated ex vivo using any suitable system and applied to patients as a periodical infusion.

Embodiments of the invention are also directed to methods of delivering a protein to the CNS of a subject, the methods including administering to a subject a peptide sequence that contains the protein to be delivered fused to peptide sequence containing a receptor-binding region of apoE, or a sequence variant, fragment, or oligomer thereof, wherein administration of the nucleic acid sequence results in expression of the fusion protein and delivery of the protein to the CNS. In some embodiments, these methods can be used to treat or prevent a neurological disorder, disease, or symptom in a subject in need thereof.

In embodiments of the invention, methods of producing a genetically engineered cell line expressing a protein of interest are provided, the methods including identifying a cell line of interest to be transformed, introducing a nucleic acid molecule into the genetic material of a cell from the cell line of interest, wherein the nucleic acid molecule encodes a fusion protein including a peptide sequence containing a receptor-binding region of apoE, or a sequence variant, fragment, or oligomer thereof, and the protein of interest, selecting for a successfully transformed cell, and cloning the transformed cell, wherein the genetically engineered cell expresses the protein of interest. In some embodiments, methods of delivering a protein to the CNS of a subject are provided, the method including administering the genetically engineered or transformed cell line to a subject, wherein administration of the genetically engineered or transformed cell line results in expression of the fusion protein and delivery of the protein to the CNS. In some embodiments, these methods can be used to treat or prevent a neurological disorder, disease, or symptom in a subject in need thereof. In some embodiments, the genetically engineered or transformed cells can be introduced by one or more of intravenous, intramuscular, oral, sublingual, buccal, parenteral, subcutaneous, intra-arterial, intraperitoneal, intracisternal, intravesical, intrathecal, transdermal, bone marrow transplantation, or rectal delivery methods. In some embodiments, the genetically engineered or transformed cells can be introduced by surgical means. In some embodiments, surgical means can include, for example, transplantation into a bone, tissue, or organ. In some embodiments, the cell line to be transformed can include, for example, bone marrow cells, hepatocytes, cells derived from embryonic stem cells, or induced pluripotent stem cells.

Embodiments of the invention are also directed to compositions that include a nucleic acid molecule, wherein the nucleic acid molecule contains a sequence encoding a fusion protein, the fusion protein including a peptide sequence containing a receptor-binding region of apoE, or a sequence variant, fragment, or oligomer thereof, and a protein to be delivered across the BBB, wherein the peptide sequence containing the receptor-binding region of apoE can be between, for example, amino acid residues 1 to 191 of apoE, between amino acid residues 25 to 185 of apoE, between amino acid residues 50 to 180 of apoE, between amino acid residues 75 to 175 of apoE, between amino acid residues 100 to 170 of apoE, between amino acid residues 125 to 165 of apoE, or between amino acid residues 130 to 150 of apoE.

Embodiments of the invention are also directed to compositions that include a nucleic acid molecule, wherein the nucleic acid molecule contains a sequence encoding a fusion protein, the fusion protein including a peptide sequence containing a receptor-binding region of apoE, or a sequence variant, fragment, or oligomer thereof, and a protein to be delivered across the BBB, wherein the fragment of the receptor-binding region of apoE includes at least 3 consecutive or substantially consecutive amino acid residues.

Embodiments of the invention are also directed to compositions that include a nucleic acid molecule, wherein the nucleic acid molecule contains a sequence encoding a fusion protein, the fusion protein including a peptide sequence containing a receptor-binding region of apoE, or a sequence variant, fragment, or oligomer thereof, and a protein to be delivered across the BBB, wherein the fragment of the peptide sequence containing a receptor-binding region of apoE can include at least 3, 4, 5, 6, 7, 8, 9, 10, 11, 12, 13, 14, 15, 16, 17, 18, 19, or 20 consecutive or substantially consecutive amino acid residues of the receptor binding domain of apoE. In some embodiments, the fragment of the peptide sequence containing a receptor-binding region of apoE can include at least one amino acid mutation, deletion, addition, or substitution. In some embodiments, the at least one substitution can be a conservative substitution. In some embodiments, the at least one amino acid addition can be an addition of a selected sequence found in a receptor-binding domain of apoE. In some embodiments, the fragment of the peptide sequence containing a receptor binding region of apoE can include a combination of two or more mutations, deletions, additions, or substitutions.

Embodiments of the invention are also directed to compositions that include a nucleic acid molecule, wherein the nucleic acid molecule contains a sequence encoding a fusion protein, the fusion protein including a peptide sequence containing a receptor-binding region of apoE, or a sequence variant, fragment, or oligomer thereof, and a protein to be delivered across the BBB, wherein the variant of the peptide sequence containing a receptor-binding domain of apoE has at least about 40%, at least about 50%, at least about 60%, at least about 70%, at least about 80%, or at least about 90% or above sequence identity to a receptor-binding domain of apoE.

Embodiments of the invention are also directed to compositions that include a nucleic acid molecule, wherein the nucleic acid molecule contains a sequence encoding a fusion protein, the fusion protein including a peptide sequence containing a receptor-binding region of apoE, or a sequence variant, fragment, or oligomer thereof, and a protein to be delivered across the BBB, wherein the variant of the peptide sequence containing a receptor-binding domain of apoE can have a sequence identity percentage of 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% to the receptor-binding domain of apoE.

Embodiments of the invention are also directed to compositions that include a nucleic acid molecule, wherein the nucleic acid molecule contains a sequence encoding a fusion protein, the fusion protein including a peptide sequence containing a receptor-binding region of apoE, or a sequence variant, fragment, or oligomer thereof, and a protein to be delivered across the BBB, wherein the oligomer can be a dimer, trimer, or tetramer.

Embodiments of the invention are also directed to compositions that include a nucleic acid molecule, wherein the nucleic acid molecule contains a sequence encoding a fusion protein, the fusion protein including a peptide sequence containing a receptor-binding region of apoE, or a sequence variant, fragment, or oligomer thereof, and a protein to be delivered across the BBB, wherein the composition can additionally include a tissue- or cell-specific promoter that can be operably linked to the sequence encoding the fusion protein, resulting in tissue-specific or cell-specific expression of the protein of interest. In some embodiments, the promoter can be an inducible promoter.

Embodiments of the invention are also directed to compositions that include a nucleic acid molecule, wherein the nucleic acid molecule contains a sequence encoding a fusion protein, the fusion protein including a peptide sequence containing a receptor-binding region of apoE, or a sequence variant, fragment, or oligomer thereof, and a protein to be delivered across the BBB, wherein the composition additionally includes a gene delivery vector. In some embodiments, the gene delivery vector can include markers or sequences that can bind to cell-specific surface receptors for targeted delivery. In some embodiments, the gene delivery vector can be a viral vector. In some embodiments, the gene delivery vector can include a lentivirus, an adenovirus, an adeno-associated virus, a retrovirus, or a self-inactivating (SIN) viral vector.

Embodiments of the invention are also directed to methods of delivering a protein to the CNS of a subject, the methods including administering to a subject compositions that include a nucleic acid molecule, wherein the nucleic acid molecule contains a sequence encoding a fusion protein, the fusion protein including a peptide sequence containing a receptor-binding region of apoE, or a sequence variant, fragment, or oligomer thereof, and a protein to be delivered across the BBB, wherein the composition additionally can include a gene delivery vector, to cells in vitro, transforming the cell's genetic material with the nucleic acid sequence encoding the fusion protein, and administering the transformed cells by intravenous, intramuscular, oral, sublingual, buccal, parenteral, subcutaneous, intra-arterial, intraperitoneal, intracisternal, intravesical, intrathecal, transdermal, bone marrow transplantation, and rectal delivery methods, wherein administration of the transformed cells results in expression of the fusion protein and delivery of the protein to the CNS.

Embodiments of the invention are also directed to methods of delivering a protein to the CNS of a subject, the methods including administering compositions that include a nucleic acid molecule, wherein the nucleic acid molecule contains a sequence encoding a fusion protein, the fusion protein including a peptide sequence containing a receptor-binding region of apoE, or a sequence variant, fragment, or oligomer thereof, and a protein to be delivered across the BBB, wherein the composition additionally can include a gene delivery vector, to a subject directly, wherein administration of the composition results in targeted delivery of the nucleic acid sequence encoding the fusion protein to a specific tissue or cell type.

Embodiments of the invention are also directed to methods of delivering a protein to the CNS of a subject, the methods including administering to a subject a peptide sequence that contains the protein to be delivered fused to peptide sequence containing a receptor-binding region of apoE, or a sequence variant, fragment, or oligomer thereof, wherein administration of the peptide sequence results in delivery of the protein to the CNS, wherein the composition is conjugated to an agent capable of mediating delivery to a target site. Embodiments of the invention are also directed to methods of delivering a protein to the CNS of a subject, the methods including administering to a subject a peptide sequence that contains the protein to be delivered fused to peptide sequence containing a receptor-binding region of apoE, or a sequence variant, fragment, or oligomer thereof, wherein administration of the nucleic acid sequence results in expression of the fusion protein and delivery of the protein to the CNS, wherein the composition is conjugated to an agent capable of mediating delivery to a target site. In some embodiments, the agent capable of mediating delivery to a target site can include, for example, nanoparticles or liposomes.

BRIEF DESCRIPTION OF THE DRAWINGS

Those of skill in the art will understand that the drawings, described below, are for illustrative purposes only. The drawings are not intended to limit the scope of the present teachings in any way.

FIG. 2A depicts a Western blot analysis of immunoprecipitated proteins. The top panel displays rabbit anti-Myc polyclonal antibodies; the bottom panel displays Coomassie blue staining of SDS gel, showing coated antibodies as loading controls. FIG. 2B depicts IDUA activity in beads and the medium after immuno-precipitation with anti-myc antibody. The same initial amounts of functional IDUA were applied to all IP reactions.

FIG. 3A depicts the IDUA enzyme activity in the medium at 2267 nmol/hr/ml for IDUA and 2230 nmol/hr/ml for IDUA3'Myc. Data were derived from two experiments; each was performed in duplicate wells. FIG. 3B depicts the co-localization of endocytosed IDUA3'Myc in the lysosome compartment.

The 3T3 cells grown on cover slides (in the lower chamber) were co-cultured with cells stably overexpressing IDUA or IDUA 3'Myc in transwells.

Figure 4:
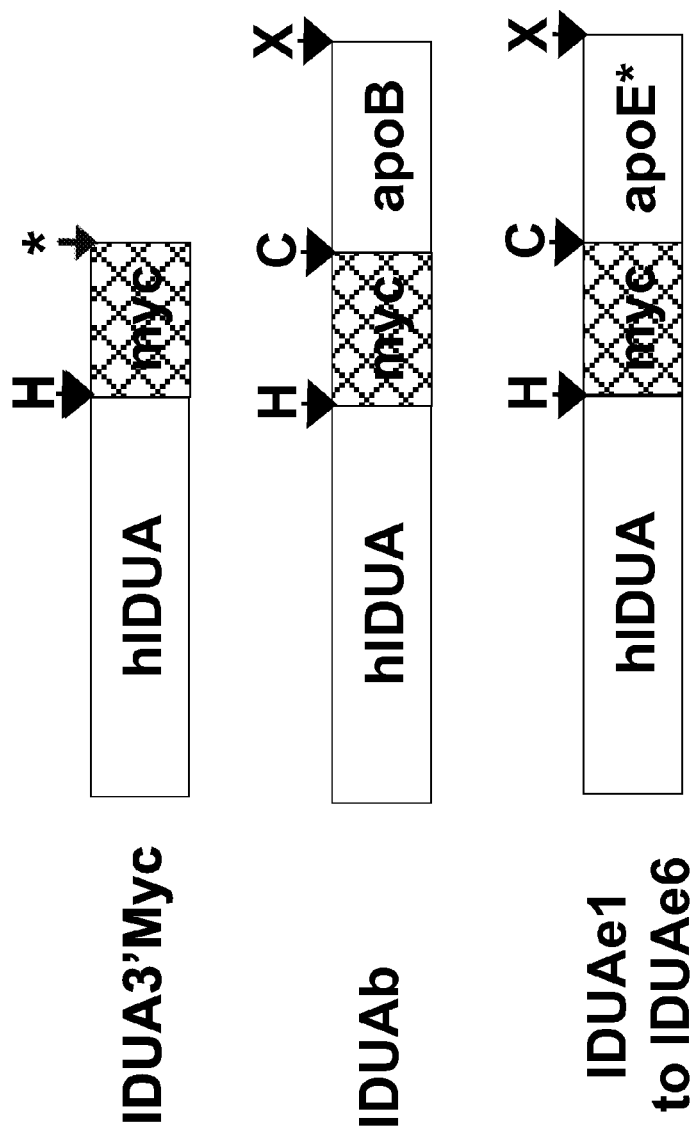

FIG. 4 depicts a diagram of modified human IDUA proteins (hIDUA) that were in-frame fused with the myc-tag and receptor-binding domain or its various derivative peptides from apolipoprotein B (apoB) or from apoE (apoE*). Arrows indicate space linkers that were encoded by restriction sites for HpaI (H), ClaI (C), XhoI (X), or a polylinker (*).

Figure 5:
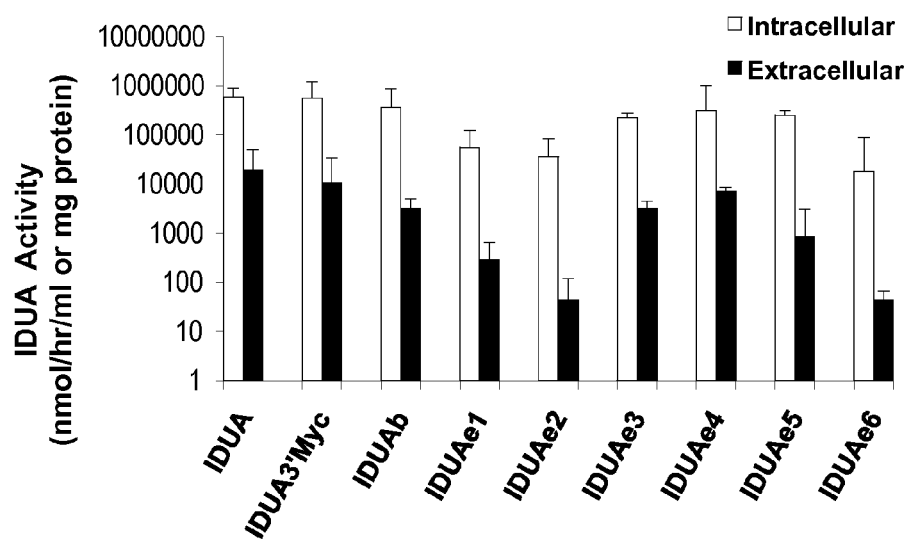
Figure 5:
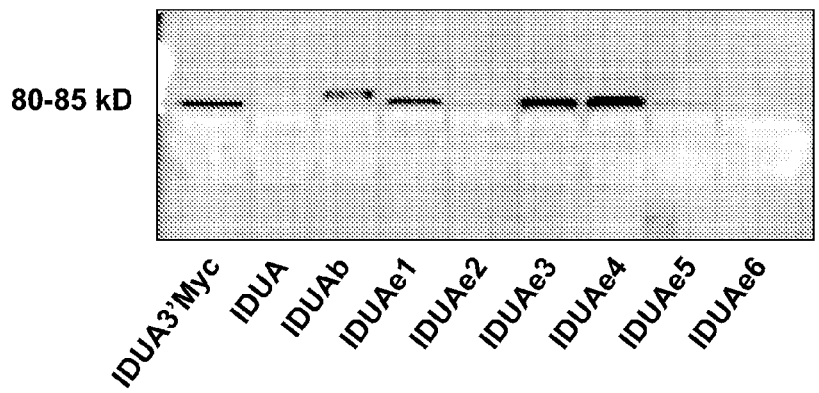

FIGS. 5A-B depict the expression and release profile of LDLRf-targeted fusion IDUA. FIG. 5A depicts IDUA catalytic activities in cell lysates or 24-hour precondition medium ($10^6$ cells/3 ml) from different 3T3 cell-based fusion IDUA-overexpressing cell lines. Stable, IDUA-expressing cell lines were obtained by co-transfecting cells with two plasmids expressing either fusion IDUA or eGFP from a CMV promoter (with transfection frequency of 15-30%) and subsequent selection of transfectants by G418. All assays were performed in triplicate. Error bars indicate standard deviations. FIG. 5B depicts a Western blot analysis of Myc-tagged fusion IDUA in medium. The rabbit anti-Myc polyclonal antibody was utilized to each lane loaded with 50 µl 24-hr precondition medium collected, as described previously. The culture medium contained 10% fetal bovine serum.

Figure 6:
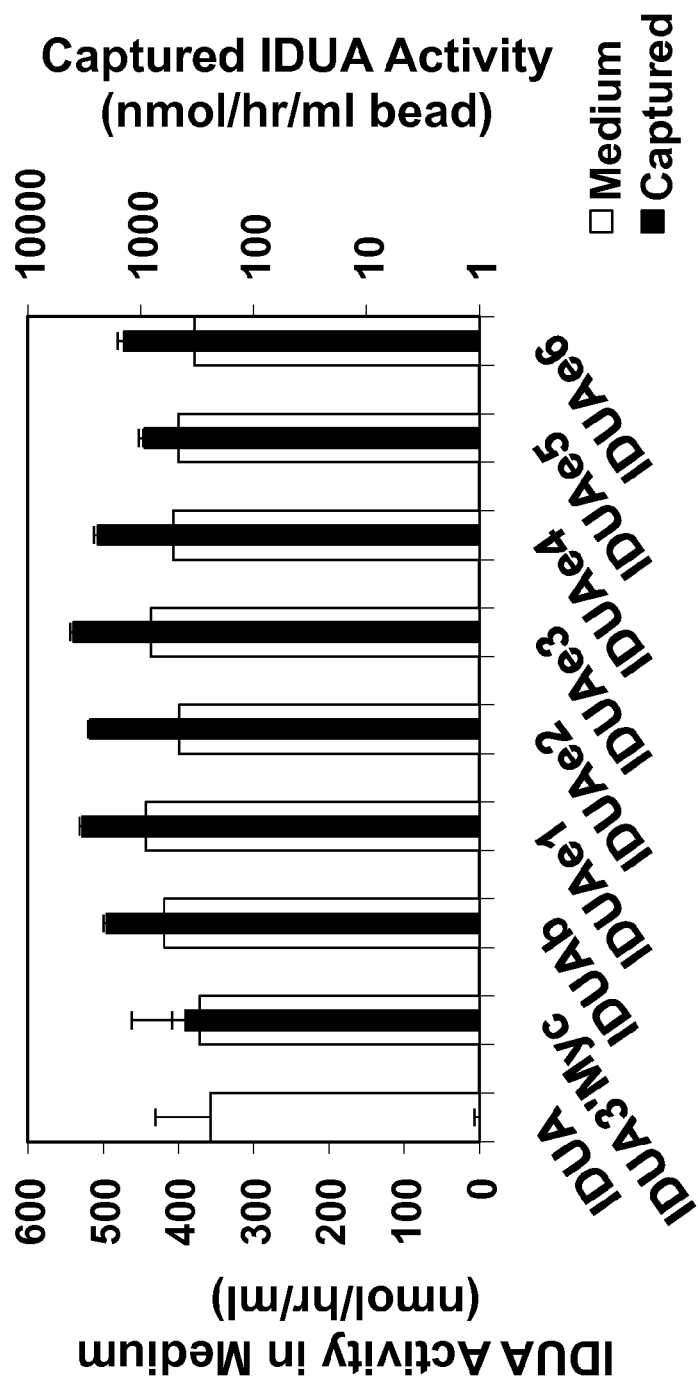

FIG. 6 depicts a bar chart illustrating the binding and catalytic ability in released form of modified IDUA. The medium was preconditioned by a 24-hour culture of different types of HEK293-based cells that stably over-expressed natural or various Myc-tagged IDUA fusion proteins that were precipitated with mouse anti-Myc monoclonal antibody, with IDUA activities indicated in open bars. IDUA activities were determined (in solid bars) using precipitated beads that had been washed three times. The experiment was performed in triplicate IP reactions with duplicate IDUA assays.

Figure 7:
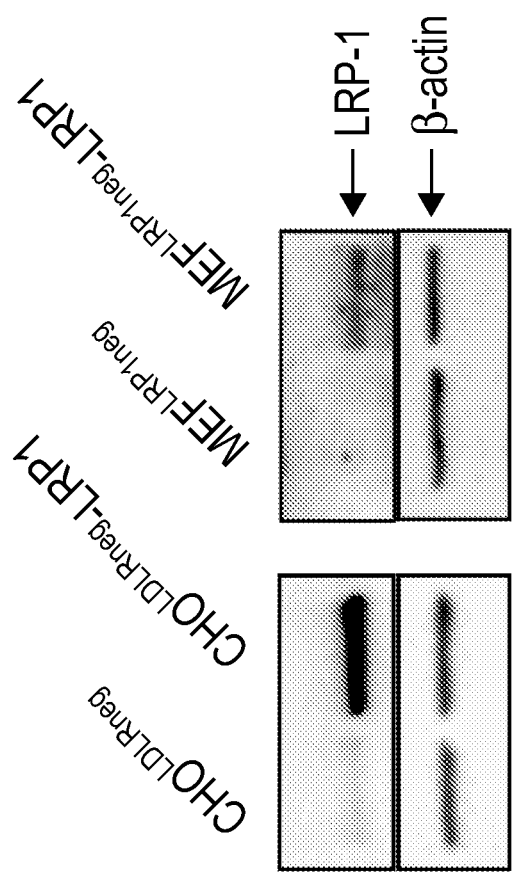

FIG. 7 depicts a photograph of the Western blot analysis for LRP1 protein expression in genetically engineered cell lines. Whole cell lysates (20 µg per lane) from indicated cell lines were loaded, and blots were developed with antibodies specific for human LRP-1 or murine β-actin (as loading controls).

Figure 8:
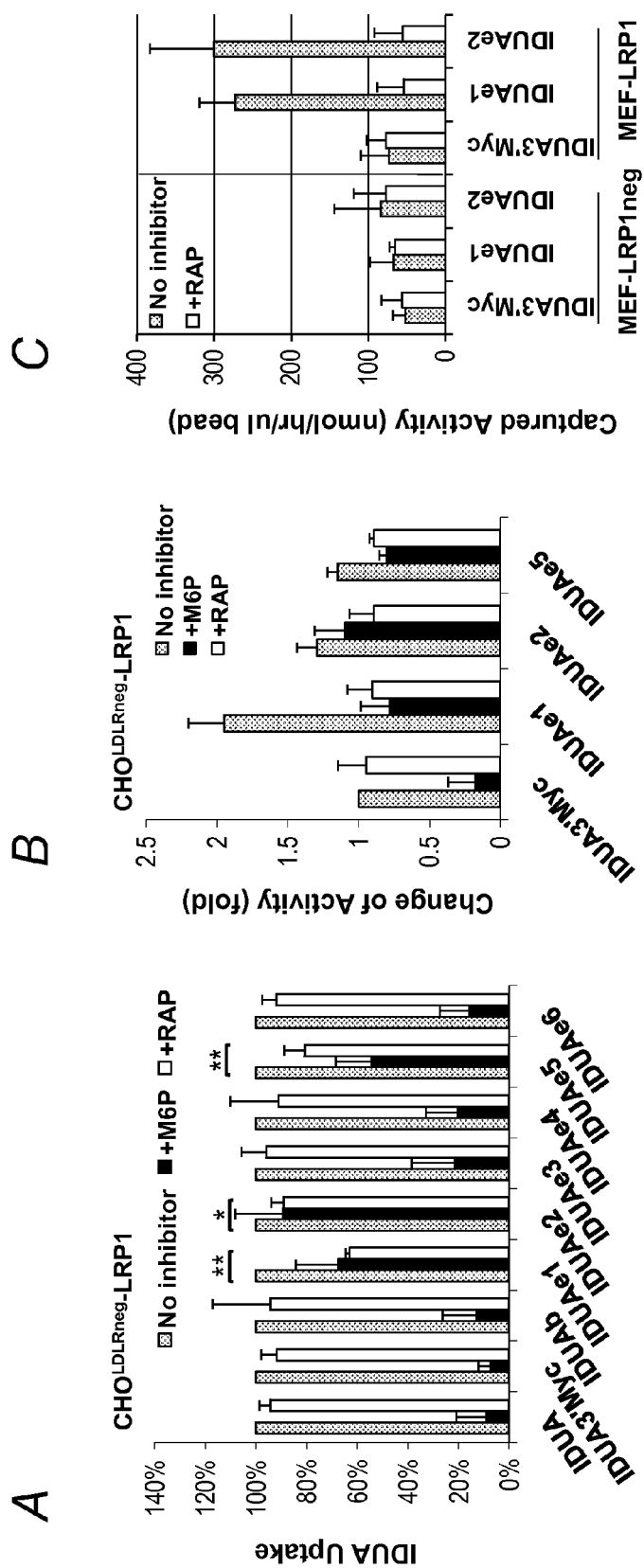

FIGS. 8A-C depict several bar charts showing the ability of reengineered IDUA proteins to introduce LRP1-mediated endocytosis in genetically modified cell lines. FIG. 8A depicts the results of uptake inhibition assays with 9 types of fusion IDUA proteins in CHO$^{LDLRneg}$-LRP1 cells after culturing cells for 2 hours with preconditioned medium containing a similar amount of reengineered fusion IDUA proteins (700-900 nmol/hr/ml) with or without the presence of M6P (1 mM) or RAP (0.5 ug/ml) inhibitor. Data were derived from 2-3 independent experiments with duplicate wells. FIG. 8B depicts results from a pause-chase assay for selected fusion IDUA candidates in CHO$^{LDLRneg}$-LRP1 cells. For the pause-chase uptake assay, CHO$^{LDLRneg}$-LRP1 cells were exposed at 4° C. for 20 min to IDUA fusion proteins of the same IDUA activity (500 nmol/ml) with or without M6P or RAP inhibitors. After multiple wash steps, cells were subsequently cultured in fresh medium at 37° C. for 1 hour, followed by IDUA enzyme assay using cell lysate as described above. IDUA activities were measured in cell lysates with normalization to protein levels determined by a Bradford assay. Data are shown as fold increase comparing to IDUA levels obtained with unmodified IDUA in the absence of any inhibitor. Two independent experiments were performed with duplicate wells for each set of the assays.

FIG. 8C depicts a comparison of selected Rb-IDUA for receptor-binding to LRP1 in cells either lacking (MEF-LRP1neg) or overexpressing (MEF-LRP1) the LRP1 receptor.

Figure 9:
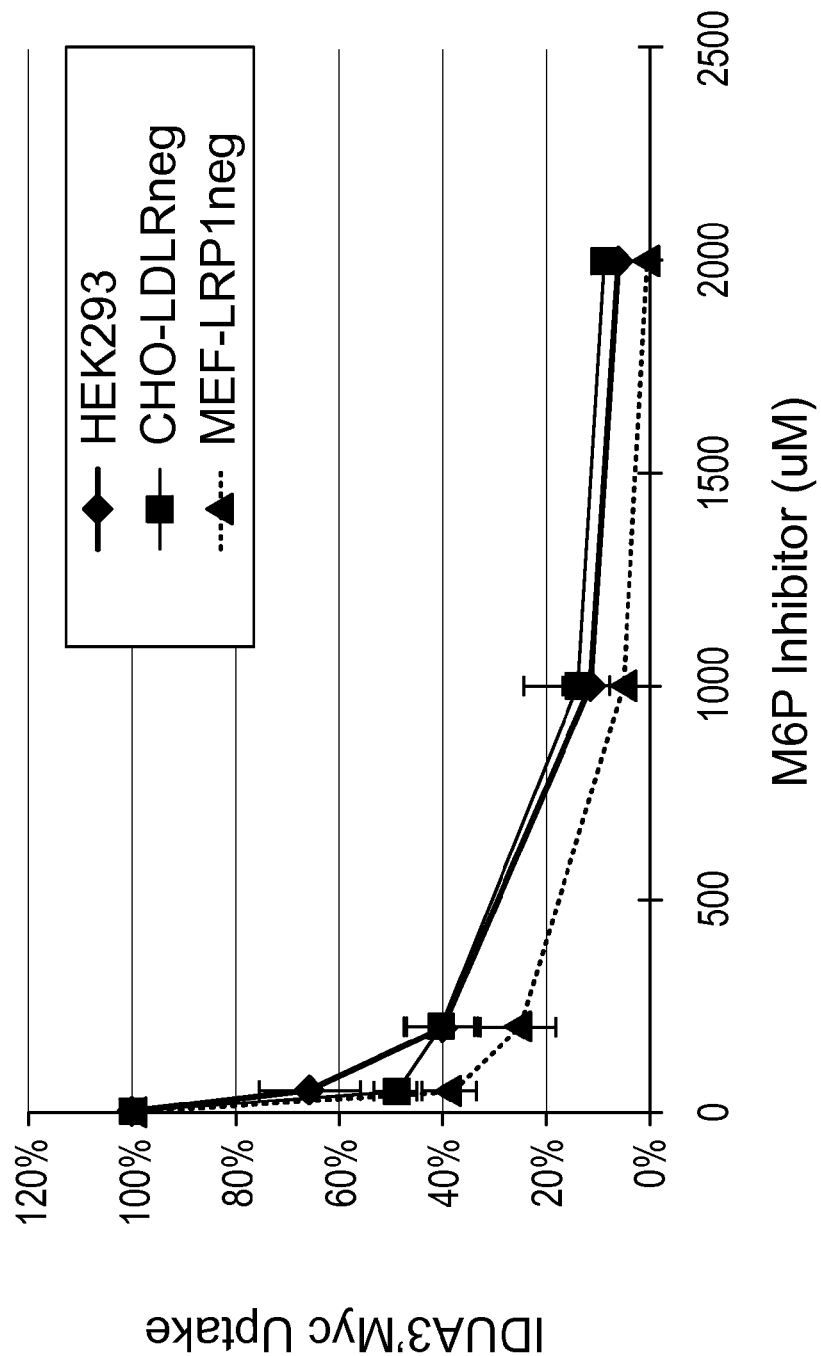

FIG. 9 depicts a plot showing the dose-dependent inhibition of IDUA3'Myc uptake in different cell lines by various amounts of M6P inhibitor. The data were derived from two individual experiments with all cell lines tested in parallel in duplicated cultures. Error bars indicate standard deviations.

Figure 10:
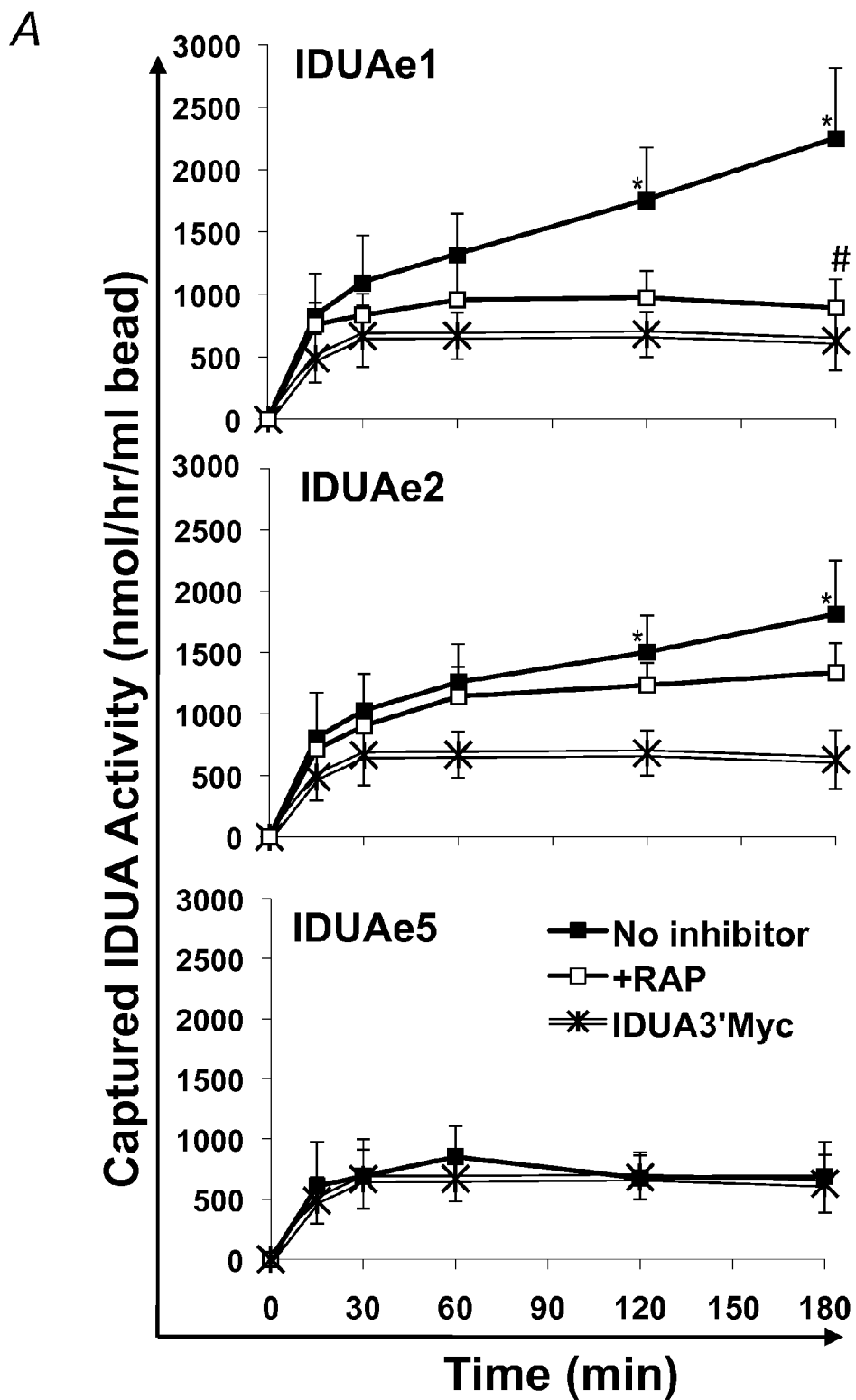
Figure 10:
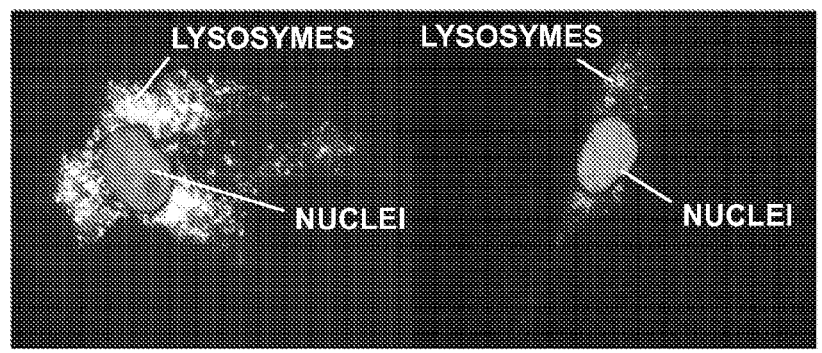
Figure 10:
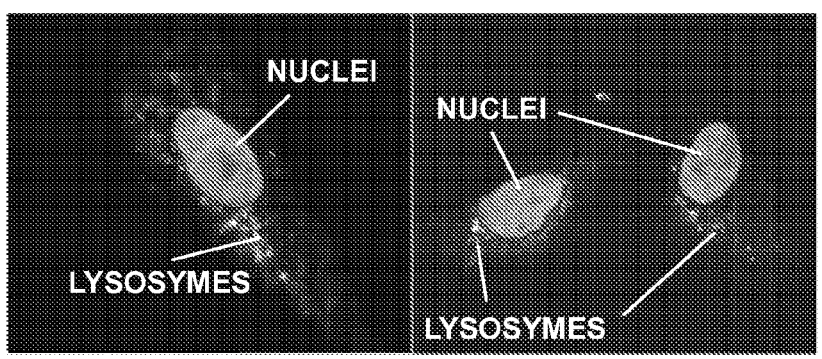
Figure 10:
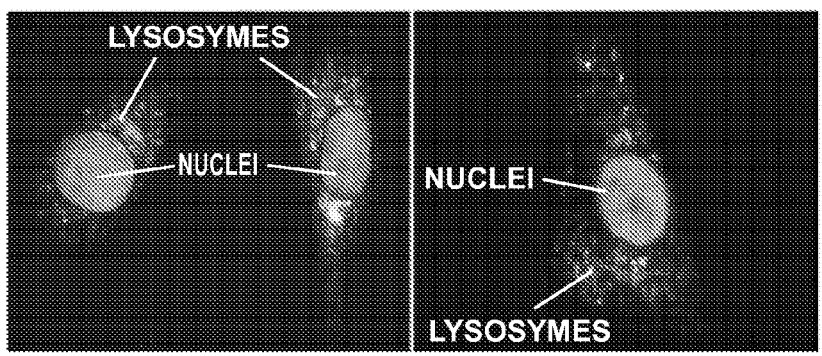

FIGS. 10A-B depict the ability of the receptor-binding peptides to facilitate LRP1-dependent transendothelial transport in vitro and to normalize lysosomal accumulation in patient fibroblasts. FIG. 10A depicts quantification of IDUA protein after exposing bovine brain microvascular endothelial cells to modified IDUA in the presence or absence of RAP competitor and subsequently immuno-precipitating IDUA protein by using Myc-antibody and quantifying by IDUA enzyme assay. Data were derived from 2-3 experiments with duplicate wells and expressed as mean±SEM. *, p<0.05 in comparing to IDUA3'Myc controls; #, p=0.08 in comparing to uptake without RAP. FIG. 10B depicts the ability of fusion IDUA candidates to normalize lysosome accumulation in fibroblasts derived from MPS patients ($F_{MPS}$), as shown by taking representative photomicrographs of lysosomal morphology following co-culturing cells with HEK293 cells that over-express natural IDUA or fusion IDUA. Immunofluorescent staining was performed with LysoTracker for lysosomes and DAPI for nuclei.

Figure 11:
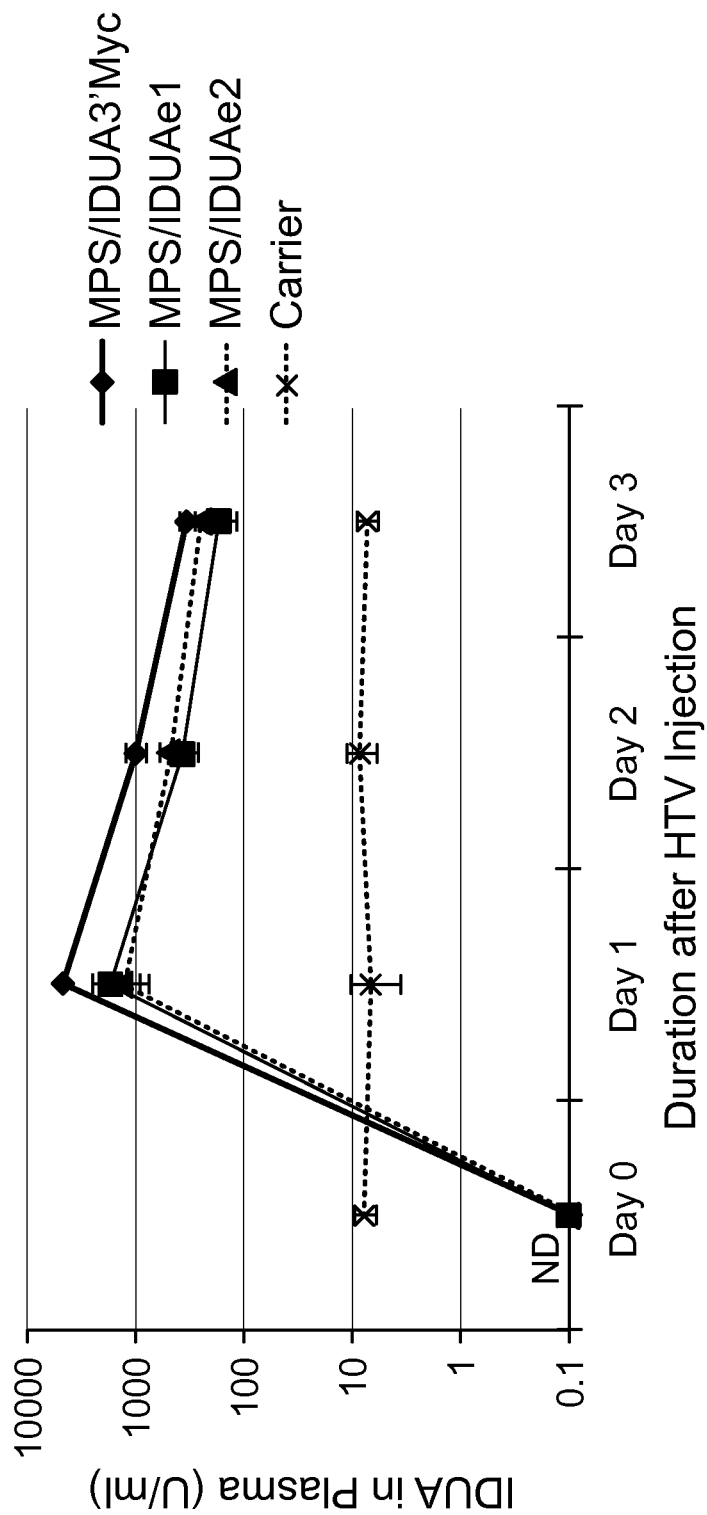

FIG. 11 depicts the time-dependent over-expression of IDUA fusion proteins in blood circulation of MPS mice after HTV injection. Blood samples were collected and analyzed at various time points from mice hydrodynamically injected with plasmids expressing fusion IDUA from a liver-specific promoter (n=4 to 8). The data were derived from 2-3 individual injection experiments with each sample assayed in duplicate reactions. Plasma IDUA levels were undetectable (ND) in un-injected MPS control mice. Error bars indicate standard deviations.

Figure 12:
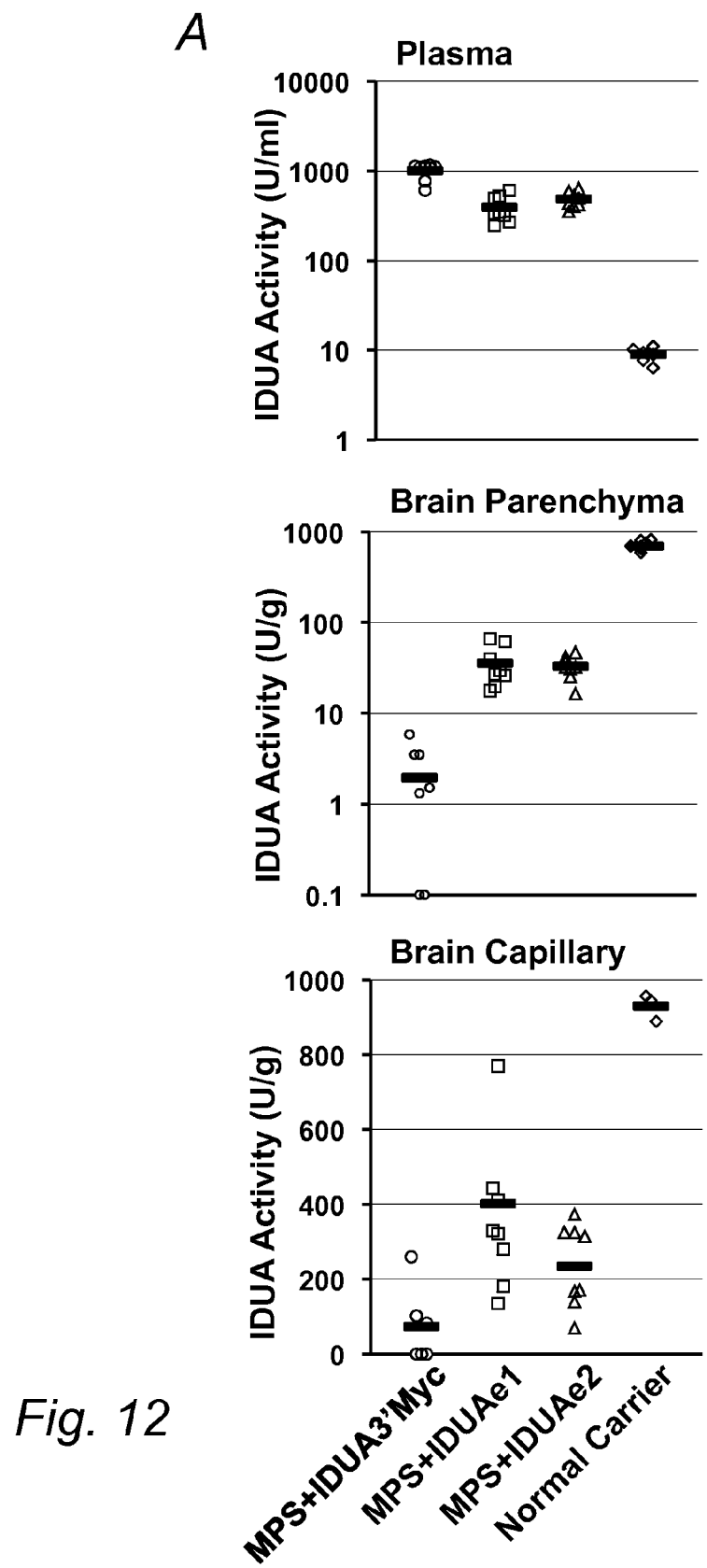
Figure 12:
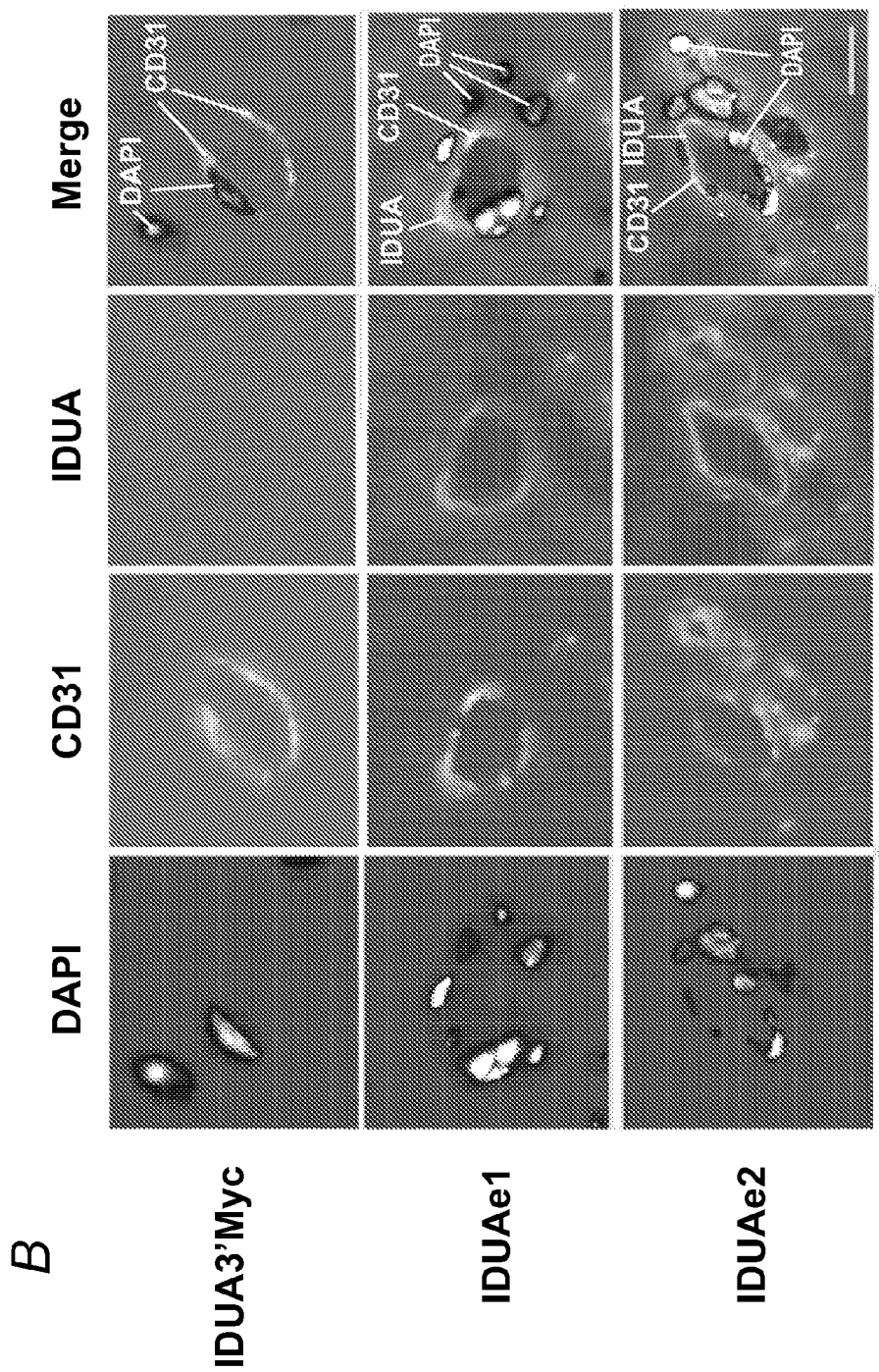
Figure 12:
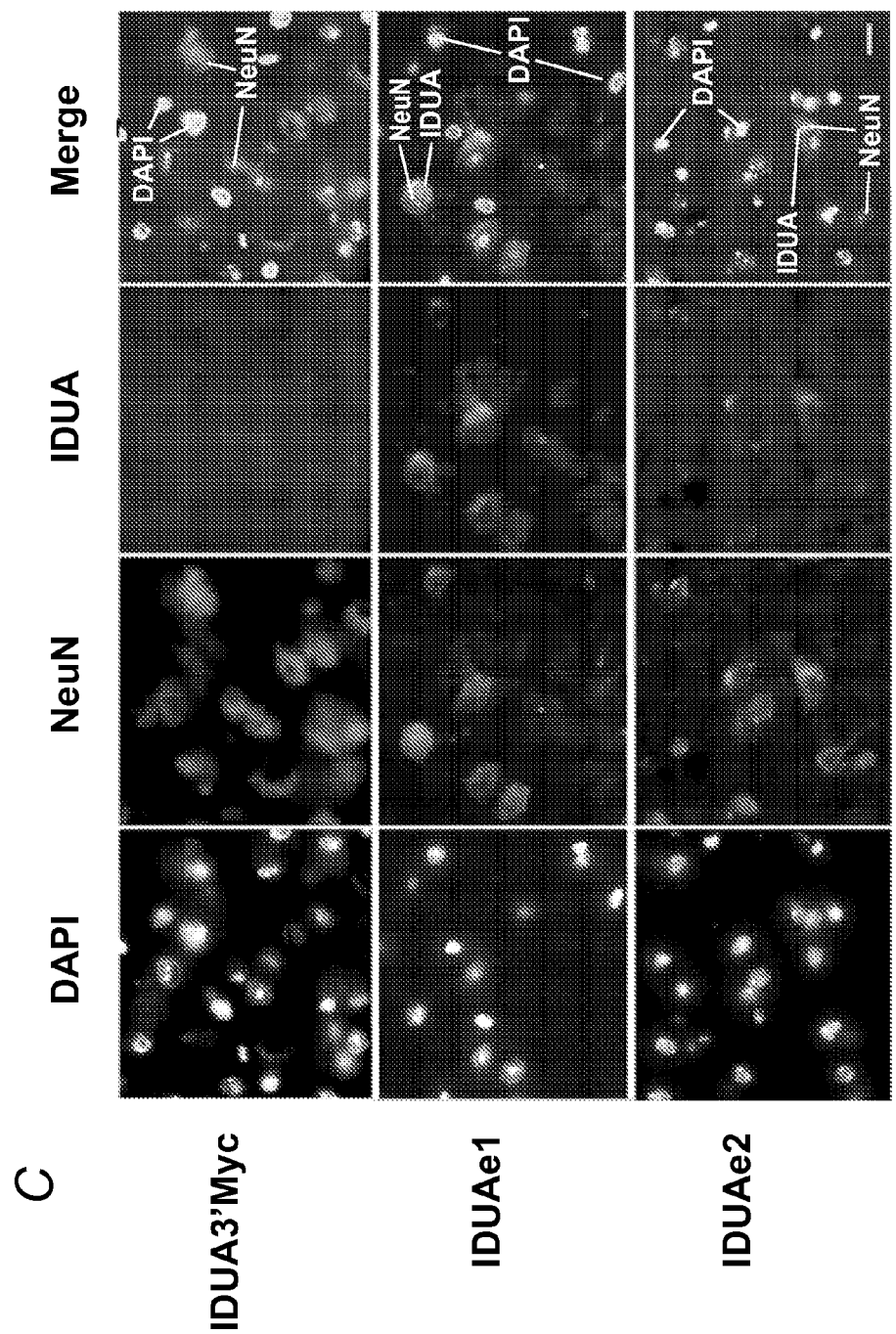
Figure 12:
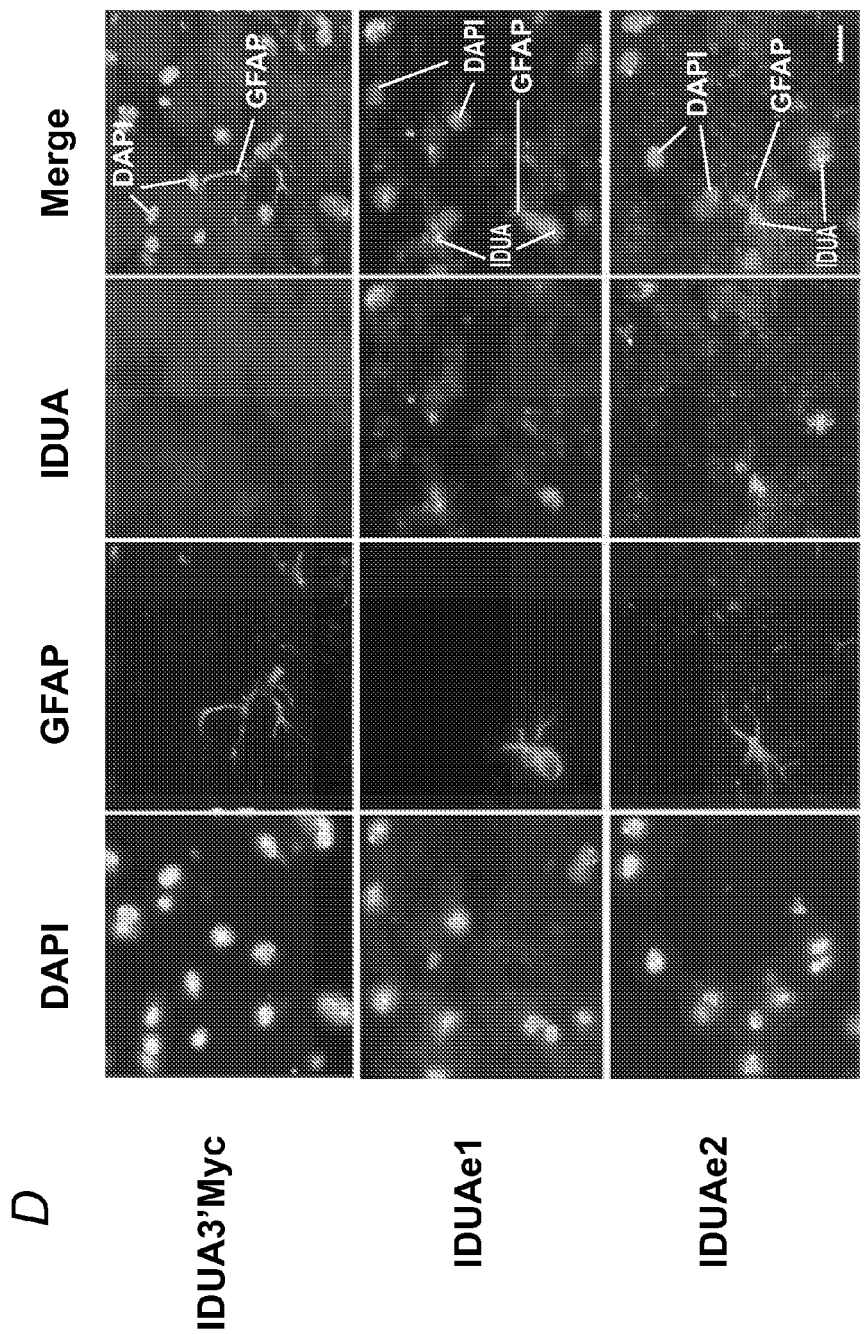
Figure 12:
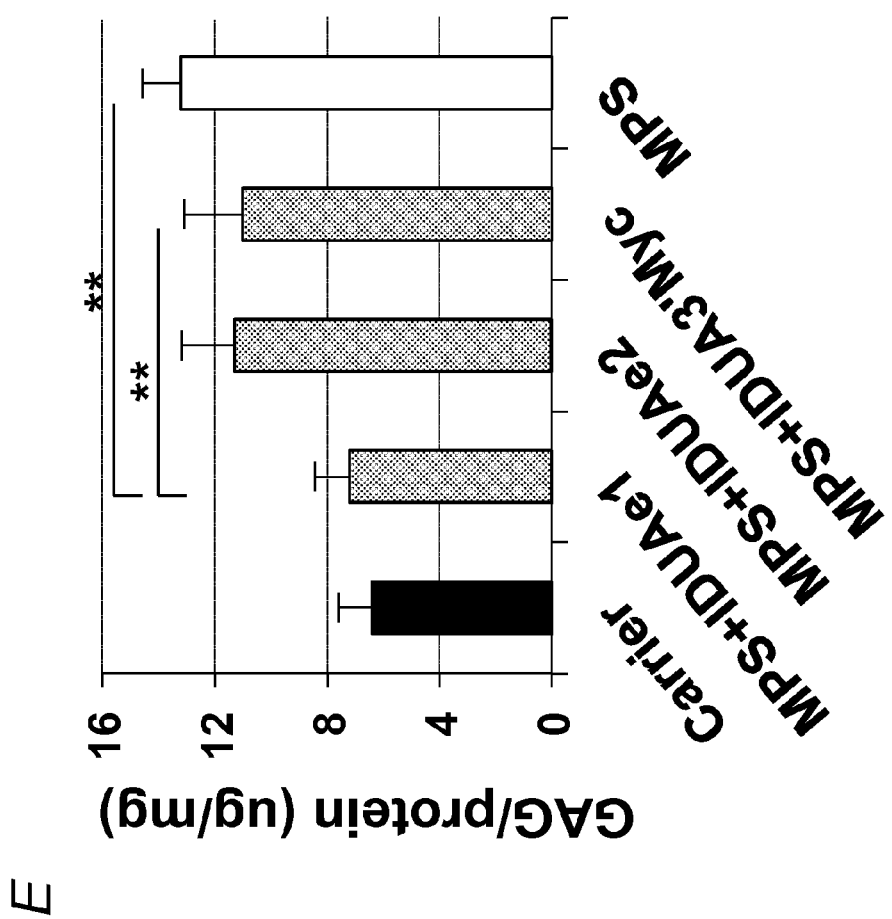

FIGS. 12A-E depict the transport of liver-generated IDUA fusion proteins in the circulation into brain parenchyma, with subsequent normalization of brain metabolic accumulation in MPS I mice. FIG. 12A depicts enzyme activities in the plasma, isolated brain capillary, and capillary-depleted brain parenchyma after HTV injection. n=7-9 mice per group; black bars represent the mean activities. FIGS. 12B-D depict representative images from immuno-fluorescence staining of brain sections. FIG. 12B depicts results from staining samples with antibodies against IDUA protein and endothelial marker (CD31). FIG. 12C depicts results from staining samples with antibodies against terminally differentiated neuron marker (NeuN). FIG. 12D depicts results from staining samples with antibodies against astrocyte marker (GFAP). All sections were counterstained with DAPI for nuclei. Scale bars, 10 μm. FIG. 12E depicts the reduction of glycosaminoglycan (GAG) accumulation in MPS brain by liver-generated Rb-IDUA. n=6-8 per group, with average plasma IDUA activities of 1771 U/ml for the IDUA3'Myc group, 808 for IDUAe1, and 456 for IDUAe2. * p<0.05, ** p<0.001, by Student's t-test in FIGS. 12A and 12E.

Figure 13:
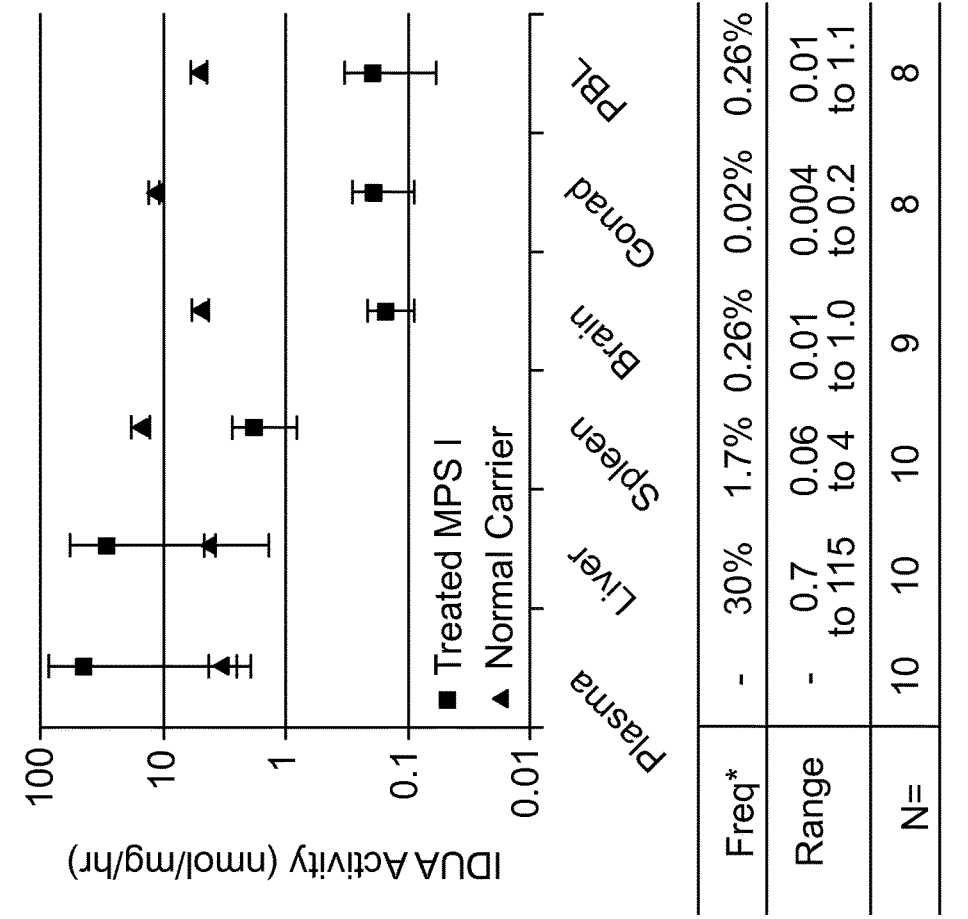
Figure 13:
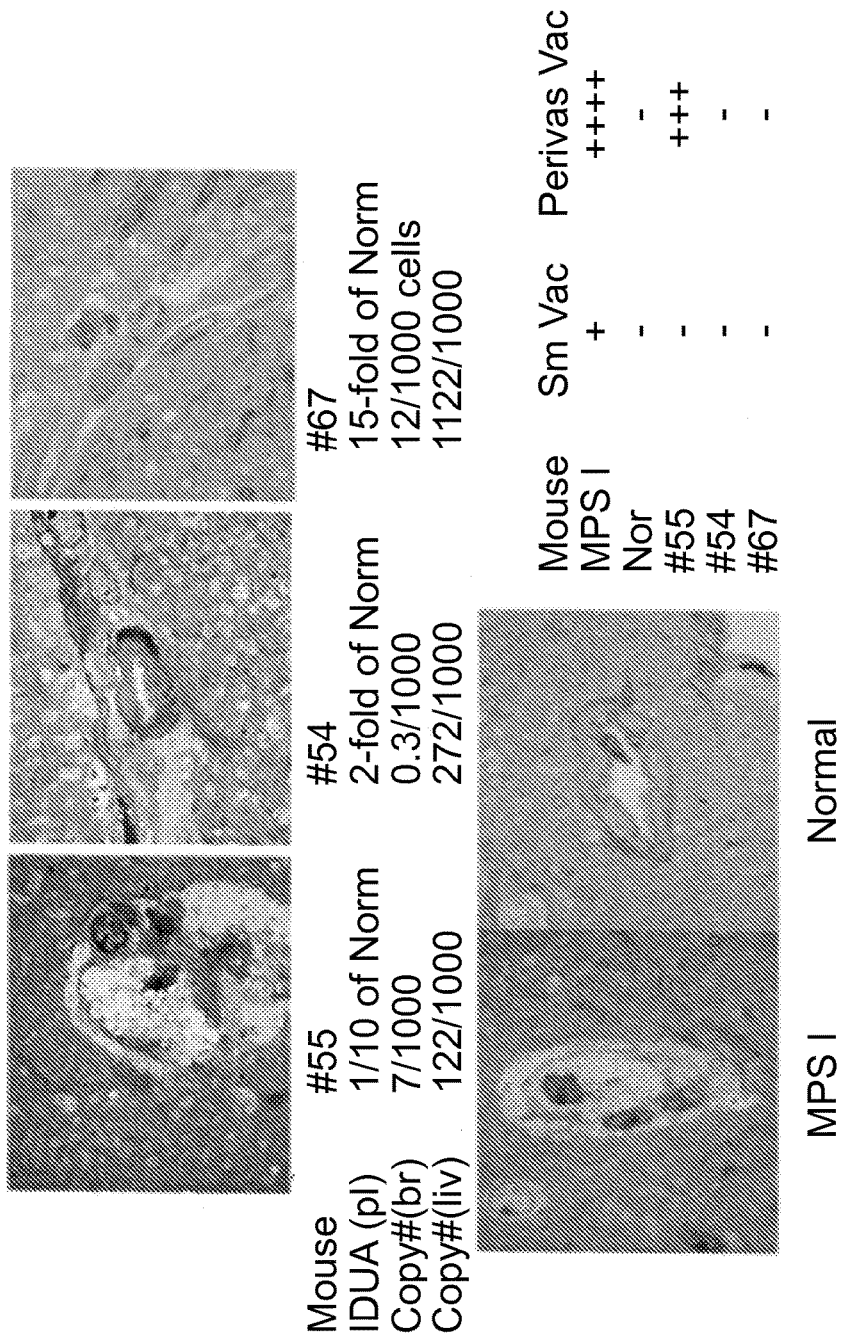
Figure 13:
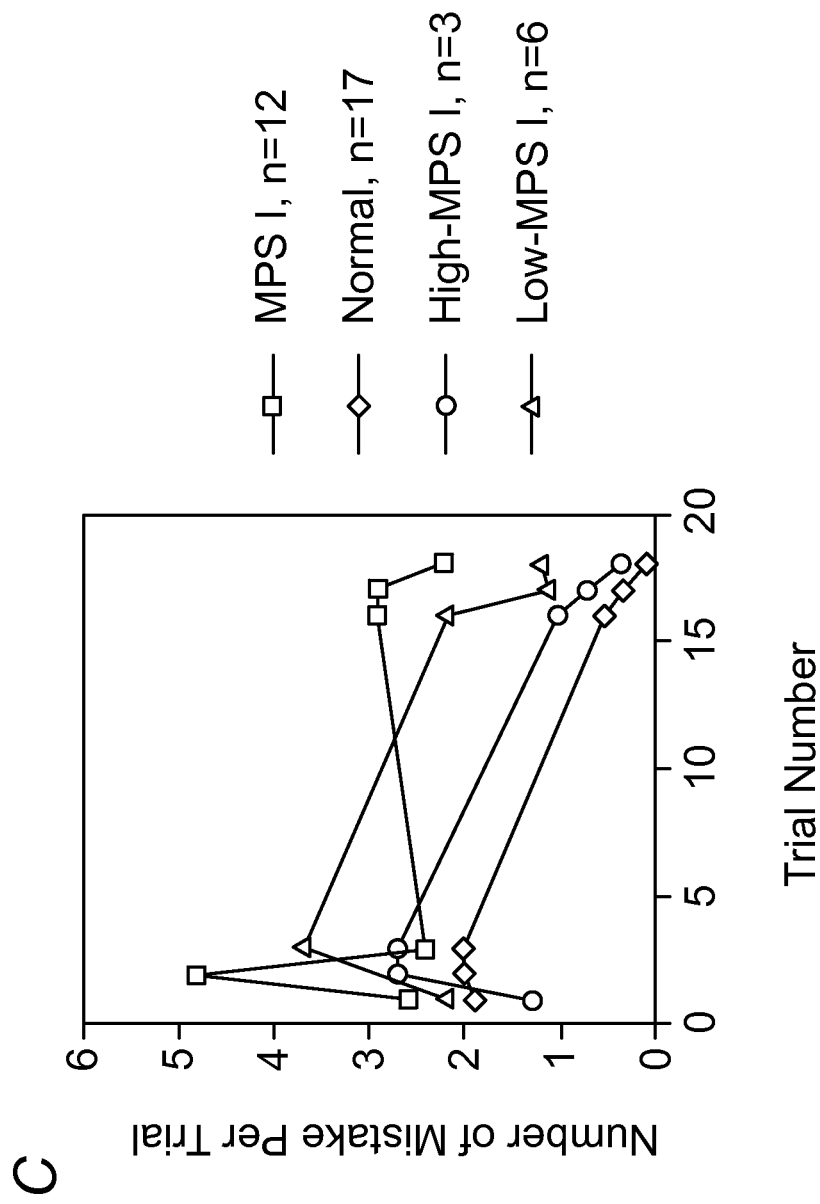

FIGS. 13A-C depict plotted data and immunohistochemical stain images illustrating neonatal gene therapy for MPS I mice. FIG. 13A depicts IDUA enzyme distribution in major organs 100 days after injection of $2 \times 10^7$ TU of a therapeutic lentiviral vector LV-PGK-IDUA. Plasma activity was expressed as nmol/ml/hr. Transgene frequency was determined by quantitative real time polymerase chain reaction (QPCR) for IDUA cDNA. FIG. 13B depicts a comparison of various levels of pathological correction in CNS via representative brain pathology in MPS I mice with low, similar, and higher than normal plasma IDUA levels 100 days after treatment. SmVac, small vacuoles; Perivas Vac, perivascular vacuoles; pl, plasma; br, brain; liv, liver. FIG. 13C depicts observed behavioral improvement in a 6-arm water maze test. Mice were allowed two daily trials of 1-minute platform learning for nine days.

DETAILED DESCRIPTION OF THE INVENTION

The restrictiveness of the blood-brain barrier (BBB) has hindered the capability of rapid and wide delivery of neurotherapeutics and diagnostic agents to the central nervous system (CNS). The BBB excludes from the brain more than 98% of all small-molecule drugs and ~100% of large-molecule therapeutics, including peptides, proteins, antibodies, RNA interference (RNAi)-based drugs, and gene vectors.

Despite great strides in the basic science of brain physiology and disease in the past decade, there is a paucity of therapies for most neurological disorders, such as mucopolysaccharidosis (MPS) type I, relatively rare LSDs and major health concerns, such as stroke and Alzheimer's disease. Efforts to develop novel approaches to cross the BBB can greatly impact the treatment of CNS diseases. The systemic delivery of neurotherapeutics via circulation would be the ideal noninvasive method for treating CNS diseases and would allow for the rapid and wide distribution of therapeutics throughout the brain, provided they can cross the BBB.

Direct brain injection approaches, such as intracranial injection and intracerebroventricular administration, have been developed to bypass the BBB. However, these methods are largely limited by practical considerations, volume restriction, and the poor diffusion of drugs/vectors from the injection site. To cross the BBB, transient BBB disruption by a variety of means can open a window for drug/vector delivery, but this can also lead to vascular pathology, astro-gliosis, and chronic neuropathologic changes in the brain. The use of liposomes and nanoparticles, as well as cationization or protein transduction domains, has been developed to exploit the lipophilicity of the BBB for brain delivery. However, these approaches lack specific brain targeting and lead to widespread absorption in all organs with consequent removal of delivered agents from the circulation. This results in a significant decrease in the ability of the drug to reach the brain at effective therapeutic concentrations.

Delivery across the BBB has been achieved by "piggy-backing" the therapeutic cargo (proteins, RNAi, or genes) onto a "targeting unit", which is either the natural substance or a monoclonal antibody as ligands for receptor-mediated BBB transport. For example, the antiviral drug azidothymidine has been delivered into the rat brain by using transferrin-PEGylated nanoparticles. However, the delivered therapeutic must compete with endogenous natural transferrin for target binding, which largely limits the transport efficiency.

Alternatively, a monoclonal antibody can bind to the receptor at an epitope different from the natural binding site; this technique has led to varying degrees of success in ferrying an attached drug, protein, antisense RNA, or plasmid DNA across the BBB in animal models. However, antibodies produced from non-human origin have the potential risk of generating an immune response in humans.

Development of effective approaches to deliver therapeutics across the BBB can provide great impact on treatment of neurological disorders. The studies described herein allow for heretofore unknown approaches for the treatment of neurological disorders, including MPS type I and major public health concerns, such as stroke and Alzheimer's disease.

Therapeutic agents can be selectively translocated across the BBB by leveraging endogenous receptor-mediated transcytosis (RMT), which exists in the BCEC for the entrance of large proteins, such as transferrin, insulin, and apolipoprotein E (apoE). Delivery systems for RMT-based BBB transport have involved liposomes, nanoparticles, or direct intravenous (IV) injection of recombinant fusion proteins. Recombinant fusion IDUA containing the heavy chain of a monoclonal antibody to the human insulin receptor has been delivered across the BBB in a Rhesus monkey 2 hours after IV protein infusion; however, the half-life of the recombinant protein was less than 2 minutes in the serum, with the least amount of fusion protein uptake found in the brain and the highest uptake in the liver. In this approach, the liver acts as a "sink" for the BBB-targeted agents by first-pass and/or receptor-mediated endocytosis, thus limiting their availability for CNS delivery. In addition, this approach is largely limited by the need of repetitive injections for any long-term effects.

The transferrin and insulin receptors have been widely explored for BBB targeting. However, the widespread high expression of these receptors in other major cell types, including hepatocytes, erythrocytes and intestinal cells, limits their capability for specific brain delivery and potential therapeutic effects.

ApoE is an important protein involved in lipid transport, and its cellular internalization is mediated by several members of the low density lipoprotein (LDL) receptor gene family, including the LDL receptor, very low-density lipoprotein receptor (VLDLR), and LDL receptor-related proteins (LRPs, including LRP1, LRP2, and LRP8). The LDL receptor is found to be highly expressed in brain capillary endothelial cells (BCECs), with down-regulated expression observed in peripheral vessels. Restricted expressions of LRPs and VLDLR have also been shown prominently in the liver and brain when they have been detected in BCECs, neurons, and glial cells. Several members of the low-density lipoprotein receptor family (LDLRf) proteins, including LRP1 and VLDLR but not LDL, are highly expressed in BBB-forming BCECs (Lillis, A. et al. *Physiol. Rev.* 88:887-918 (2008); Ueno, M. et al. *Curr. Med. Chem.* 17:1125-38 (2010)). These proteins can bind apoE to facilitate their transcytosis into the abluminal side of the BBB.

In addition, receptor-associated protein (RAP), an antagonist as well as a ligand for both LRP1 and VLDLR, has been shown to have higher permeability across the BBB than transferrin in vivo and in vitro (Pan, W. et al. *J. Cell Sci.* 117:5071-8 (2004)), indicating that these lipoprotein receptors (LDLRf) can represent efficient BBB delivery targets despite their lower expression than the transferrin receptor. Furthermore, gene expression mapping in the brains of adult mice has demonstrated high and widespread expression of LRP1 and VLDLR throughout brain parenchyma (found at http <colon slash slash> www <dot> brain-map <dot> org), indicating that a secondary targeting system exists for further distribution of transcytosed proteins/therapeutics within the brain.

As disclosed herein, experiments to develop a protein containing a fusion of the LDLRf receptor-binding domain (Rb) of apoE to a model protein, α-L-iduronidase (IDUA), illustrate the ability of the fusion protein to bind LDLRf and transcytose to the central nervous system (CNS). Furthermore, synergistic CNS benefits can be achieved by delivering this fusion protein to a depot organ/tissue, such as the liver, or by delivering hematopoietic stem cells (HSC) via lentiviral (LV)-mediated gene transfer to a depot organ/tissue.

The LDLRf system has been investigated for therapeutic delivery to the brain. One study demonstrated that the receptor-binding domain of apolipoprotein B (apoB) can facilitate fusion protein transport across the BBB (Spencer, B. and Verma, I. *Proc. Natl. Acad. Sci. U.S.A.* 104:7594-9 (2007)). By fusing a secreted form of GFP or glucocerebrosidase (a lysosomal protein responsible for Gaucher disease) to the receptor-binding domain of apoB, the modified protein can be detected by immunostaining in neurons and astrocytes after intraperitoneal injection of LV vector. Binding to LDLRf can therefore mediate fusion protein transcytosis across the BBB. However, apoB binds only to LDLR and has negligible affinity to LRP1 or other LDLRf proteins (Hui, D. et al. *J. Biol. Chem.* 256:5646-55 (1981)). Another study showed that the conjugation of apoE to nanoparticles can trigger LDLRf-mediated transcytosis across the BBB in mice (Kreuter, J. et al. *J. Control. Release* 118:54-8 (2007)). However, the use of the entire apoE molecule may potentially interfere with its natural biological functions, including apoE isoform-specific effects on Alzheimer disease (Bu, G. *Nat. Rev. Neurosci.* 10:333-44 (2009)).

Use of the LDLRf-mediated transcytosis BBB-targeted protein delivery therefore requires the identification of one or more receptor-binding peptide sequence (Rb) from apoE in a fusion protein setting, as well as the evaluation of its ability for receptor binding, internalization, brain delivery, and biological function of the cargo protein in vivo. Use of only the receptor-binding region of apoE, rather than the entire apoE molecule, as the targeting unit to deliver the IDUA protein across the BBB can minimize any potential interference with the natural physical functions of apoE. In addition, the IDUA protein can facilitate further CNS distribution of enzyme and protein products delivered to the CNS by secondary distribution through LRP1-mediated pathways that bypass the BBB. For example, direct brain injection of a viral vector expressing a lysosomal enzyme has been used to treat MPS type III. Progress has been made on enzyme replacement treatment using, for example, intrathecal injection.

Accordingly, studies were carried out to investigate the utilization of the LDLRf-mediated transcytosis system for CNS delivery.

As described herein, a potent receptor-binding peptide (Rb) derived from apoE was identified, and the ability to translocate protein across the BBB into the mouse brain when engineered as fusion proteins was demonstrated by in vitro screening and in vivo evaluation. This method can therefore function to selectively open the BBB for therapeutic agents when engineered as a fusion protein. This peptide can be readily attached to diagnostic or therapeutic agents without jeopardizing their biological functions or interfering with the important biological functions of apoE due to the utilization of the Rb domain of apoE, rather than the entire apoE protein.

The lysosomal enzyme IDUA was utilized for biological and therapeutic evaluation in a mouse model with CNS deficits. Two Rb-IDUA candidates were identified by in vitro screening for desirable receptor-mediated binding, endocytosis, and transendothelial transport, as well as appropriate lysosomal enzyme trafficking and biological function. In vivo studies showed that peripheral Rb-IDUA generated from hepatic-expression resulted in elevated enzyme activities in brain tissues. Immunofluorescence analysis revealed protein delivery to non-endothelium perivascular cells, neurons, and astrocytes in the diseased brain. The therapeutic potential was demonstrated by metabolic correction in brain glycosaminoglycan (GAG) accumulation after short-term systemic protein delivery The BBB-targeted, LRP1-binding Rb-tag developed and described herein provides systemic drug/protein delivery by adapting a receptor-mediated transport system to the BBB. This therapeutic strategy combines protein engineering, gene therapy, and bone marrow transplantation for prolonged systemic IDUA delivery across the BBB for CNS correction in MPS type I and other neurological disorders. This pathway is also an alternative uptake pathway that can facilitate further/secondary distribution within the brain after the agents reach the CNS due to the widespread expression of LDLRf members in brain parenchyma. Regardless of application strategies, e.g., enzyme replacement therapy or cell-based, gene-based therapy, both the quantity and distribution of therapeutics within the brain parenchyma will have a significant impact on the clinical outcome of disease treatment. The method described herein can open the "gate" of the BBB specifically to large-molecule neurotherapeutics.

As used herein, "subject" can refer to any living creature, typically an animal, preferably a mammal, and more preferably a human.

As used herein, "operably linked" refers to a juxtaposition of two or more components, wherein the components so described are in a relationship permitting them to function in their intended manner. For example, a promoter is operably linked to a coding sequence if it acts in cis to control or modulate the transcription of the linked sequence. Generally, but not necessarily, the nucleic acid sequences that are "operably linked" are contiguous and, where necessary to join two protein coding regions or in the case of a secretory leader, contiguous and in reading frame. However, although an operably linked promoter is generally located upstream of the coding sequence, it is not necessarily contiguous with it. Operably linked enhancers can be located upstream, within, or downstream of coding sequences and at considerable distances from the promoter. Linking is accomplished by recombinant methods known in the art, e.g., using PCR methodology, by annealing, or by ligation at convenient restriction sites. If convenient restriction sites do not exist, then synthetic oligonucleotide adaptors or linkers are used in accord with conventional practice.

LDLR Family Binding Domain

In some embodiments, the fusion protein includes a peptide sequence containing the LDLRf receptor-binding domain (Rb) of apoE, or a fragment, variant, or oligomer thereof. An exemplary receptor-binding domain can be found in the N-terminus of apoE, for example, between amino acid residues 1 to 191 of apoE, between amino acid residues 25 to 185 of apoE, between amino acid residues 50 to 180 of apoE, between amino acid residues 75 to 175 of apoE, between amino acid residues 100 to 170 of apoE, or between amino acid residues 125 to 165 of apoE. An exemplary receptor-binding domain can include, for example, amino acid residues 130 to 150 of apoE.

As used herein, a fragment of the peptide sequence containing the receptor-binding domain apoE can include at least 3 consecutive or substantially consecutive amino acid residues. For example, a fragment can include at least 3, 4, 5, 6, 7, 8, 9, 10, 11, 12, 13, 14, 15, 16, 17, 18, 19, or 20 consecutive or substantially consecutive amino acid residues of the receptor-binding domain of apoE. The length of the fragment can be appropriately changed depending on the purpose. Mutations, truncations, additions, deletions, substitutions, and other alterations of the sequence are included in the definition of fragment, provided some degree of the biochemical activity for transport across the BBB is preserved.

As used herein, substantially consecutive amino acid residues are those that are not literally consecutive. Substantially consecutive amino acid residues can include amino acids that are separated by one or more amino acid residues along the length of the polypeptide chain or amino acids that are separated by one or more amino acid residues spatially within a receptor binding domain.

In some embodiments, the peptide sequence containing the receptor-binding domain of apoE can include at least one amino acid mutation, deletion, addition, or substitution. In some embodiments, the amino acid substitutions can be a combination of two or more mutations, deletions, additions or substitutions. In some embodiments, the at least one substitution is a conservative substitution. In some embodiments, the at least one amino acid addition includes addition of a selected sequence already found in the receptor-binding domain of apoE. A person of ordinary skill in the art will recognize suitable modifications that can be made to the sequence while retaining some degree of the biochemical activity for transport across the BBB.

A table of conservative substitutions that can be considered for embodiments of the invention is provided in Table 1.

TABLE 1

Conservative amino acid substitutions.

| | |
|---|---|
| Group 1 | Ile, Leu, Val, Ala, Gly |
| Group 2 | Trp, Tyr, Phe |
| Group 3 | Asp, Glu, Asn, Gln |
| Group 4 | Cys, Ser, Thr, Met |
| Group 5 | Pro |
| Group 6 | His, Lys, Arg |

As used herein, a variant of the peptide sequence containing the receptor-binding domain of apoE can have at least about 40%, at least about 50%, at least about 60%, at least about 70%, at least about 80%, and at least about 90% or above sequence identity to receptor-binding domain of apoE. Exemplary sequence identity percentages include 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, and 100%. (Note: we shall also include variants such as tandem repeats of Rb. In fact, two Rb candidates we identified are tandem repeat of the same fragment.)

As used herein, an oligomer of the peptide sequence containing the receptor-binding domain of apoE can be a dimer, trimer, or tetramer. In some embodiments, the oligomer is a heteromer.

Suitable Proteins for Delivery Across the BBB

Any protein that can be modified by molecular cloning at any position without loss of its relevant biochemical activity can be included in compositions as herein disclosed. Depending on the protein's secondary structure, the fusion insertion site can be at the N-terminus, C-terminus, or anywhere within the protein sequence as long as the protein's relevant biochemical activity remains intact and the added peptide domain is exposed as an epitope for receptor binding. Using standard molecular biology techniques and assays, the skilled artisan will understand what proteins are suitable for expression and use in the compositions described herein.

Methods of Delivery and Treatment

The compositions disclosed herein can be used in methods of treating or preventing a neurological disorder, disease, or symptom in a subject in need thereof.

In some embodiments, a composition comprising a fusion protein as disclosed herein can be directly administered to a subject, wherein administration of the composition results in delivery of the protein of interest across the BBB.

In some embodiments, a composition comprising a nucleic acid encoding a fusion protein as disclosed herein can be directly administered to a subject, wherein administration of the composition results in expression of the protein of interest and delivery of the protein across the BBB. In some embodiments, the composition can also include a tissue-specific or cell-specific promoter that is operably linked to the sequence encoding the fusion protein, resulting in tissue-specific or cell-specific expression of the protein of interest.

Routes of Delivery

Delivery of compositions comprising a fusion protein as disclosed herein, or a nucleic acid molecule encoding the same, to a subject in need thereof can be carried out by a variety of means, including, but not limited to, intravenous, intramuscular, and oral. Additional routes of administration include sublingual, buccal, parenteral (including, for example, subcutaneous, intramuscular, intra-arterial, intraperitoneal, intracisternal, intravesical, intrathecal, or intravenous), transdermal, and rectal points of entry. Such routes of entry are also applicable to cells that are transformed by gene therapy methods as described herein.

Gene Therapy Methods

Embodiments of the invention are also related to compositions containing a gene delivery vector, wherein the vector includes a nucleic acid sequence encoding a fusion protein as disclosed herein.

In some embodiments, compositions comprising the gene delivery vector can be administered to cells in vitro to transform the cell's genetic material with the nucleic acid sequence encoding the fusion protein. Cells that can be transformed include bone marrow cells, hepatocytes, cells derived from embryonic stem cells, induced pluripotent stem cells, and the like. Transformed cells can be selected using standard methods of selection (such as, for example, antibiotic selection or GFP expression combined with FACS), and selected cells can be clonally expanded in sufficient numbers for introduction into a subject in need thereof. The transformed cells can be introduced by way of any of the routes of delivery described herein. In some embodiments, the transformed cells are introduced by surgical means, such as, for example, transplantation into a bone, specific tissue, or organ.

In some embodiments, compositions comprising the gene delivery vector can be administered to a subject directly, wherein administration of the composition results in targeted delivery of the nucleic acid sequence encoding the fusion protein to a specific tissue or cell type. Such gene delivery vectors can include markers or sequences that can bind to cell-specific surface receptors for targeted delivery. Once endocytosed into the target cell or cells, the nucleic acid sequence can be translated into protein, resulting in expression and secretion of the protein of interest for circulation and delivery across the BBB.

The gene delivery vector can be a viral vector, such as, for example, a lentivirus, an adenovirus, an adeno-associated virus, or a retrovirus. In some embodiments, the viral vector can be a self-inactivating (SIN) viral vector.

In some embodiments, the nucleic acid sequence encoding the fusion protein is operably linked to a promoter. In some embodiments, the promoter is an inducible promoter.

Enzyme Replacement Therapy Methods

Embodiments of the invention are also related to the administration to a subject of a fusion protein as disclosed herein via enzyme replacement therapy. In some embodiments, the fusion protein can be generated ex vivo using any suitable system and applied to patients as a periodical infusion. In some embodiments, the suitable system can include the use of recombinant lysosomal enzymes. In some embodiments, enzyme replacement therapy can involve intrathecal injection.

Treatment of Diseases or Conditions

Embodiments of the invention are also related to use of compositions comprising a fusion protein as described herein to treat a disease or condition that is affected by or affects or is located within the CNS, the brain, the spinal cord, or any other portion of the CNS. In some embodiments, the disease or condition can be a lysosomal storage disease.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

EXAMPLES

The following non-limiting examples are provided to further illustrate embodiments of the invention disclosed herein. It should be appreciated by those of skill in the art that the techniques disclosed in the examples that follow represent approaches that have been found to function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

Determining the Accessibility of IDUA Protein for Genetic Manipulation

Alpha ($\alpha$)-L-iduronidase protein (IDUA, EC3.2.1.76) is synthesized in the endoplasmic reticulum as a 653-amino-acid precursor, which undergoes post-translational glycosylation and extensive proteolytic processing to produce at least 10 polypeptides as a result of normal residence in the endosome-lysosome compartments. LRP1-mediated brain delivery was investigated by utilizing a lysosomal enzyme IDUA fused to Rb peptides to track and evaluate biological functions of the fusion protein in an enzyme-deficient mouse model of mucopolysaccharidosis type I (MPS I), one of the most common lysosomal storage diseases with CNS deficits (Pan, D. Curr. Pharm. Biotechnol. 12:884-96 (2011)).

Protein structural analysis with 3D tools has indicated a potential signal peptide located at the N-terminus and a fibronectin-like domain near the C-terminus (Swiss-Prot #P35475). To determine the accessibility of IDUA for genetic modification, a human myc-tag (Table 2) was fused in-frame to the 5'- or 3'-end of the human IDUA coding sequence (Wang, D. et al. *Proc. Natl. Acad. Sci. U.S.A.* 106:19958-63 (2009)).

TABLE 2

Peptide sequence design as receptor-binding domain candidates for fusion IDUA construction.

| Rb ID | Size (Monomer × N) | apoE Precursor Location | Accession # |
|---|---|---|---|
| myc | 10 + 5* | residues 410-419 | P01106 |
| apoB | 39 | residues 3371-3409 | P04114 |
| apoE1 | 18 (9 × 2) | residues 159-167 | P02649.1 |
| apoE2 | 30 (15 × 2) | residues 159-173 | P02649.1 |
| apoE3 | 17 | residues 151-167 | P02649.1 |
| apoE4 | 20 | residues 148-167 | P02649.1 |
| apoE5 | 34 (17 × 2) | residues 151-167 | P02649.1 |
| apoE6 | 40 (20 × 2) | residues 148-167 | P02649.1 |

*A 5-amino acid space-linker (IDILE) was included following myc-tag because of the addition of a polylinker upstream to the stop codon.

The IDUA5' myc and IDUA3' myc fusion cassette were derived by TOPO-cloning to introduce a human c-myc tag (410-419) and a flanking polylinker in-frame at 5', right after the start codon, or at 3', immediately before the stop codon of human IDUA cDNA (Pan, D. et al. *Gene Ther.* 7:1875-83 (2000)). All 7 Rb coding sequences, as shown in Table 2, were inserted between the Cla I and Xho I sites within the polylinker of IDUA3' myc. The plasmids over-expressing different IDUA fusion candidates from the CMV promoter were constructed by insertion into pcDNA 3.1 (Invitrogen, Carlsbad, Calif.) between the Hind III and XbaI sites. To restrict gene expression in the liver, the pBS-HCRHPI-A plasmid (Miao, C. et al. *Hum. Gene Ther.* 14:1297-1305 (2003)) was utilized by subcloning selected Rb-IDUA coding sequences into the NdeI and EcoRV sites. The pcDNA3.1/Zeo-LRP1 was generated by inserting the full-length cDNA of LRP-1 (Accession #NM_002332.2) into the SHO I and Not I sites of pcDNA3.1/Zeo. The accuracy of all plasmids was verified by sequence analysis. The modified IDUA sequences were then evaluated for catalytic function, enzyme trafficking and re-uptake, and retention of Myc-tag binding function.

Intracellular and Extracellular Enzyme Activity.

Figure 1:
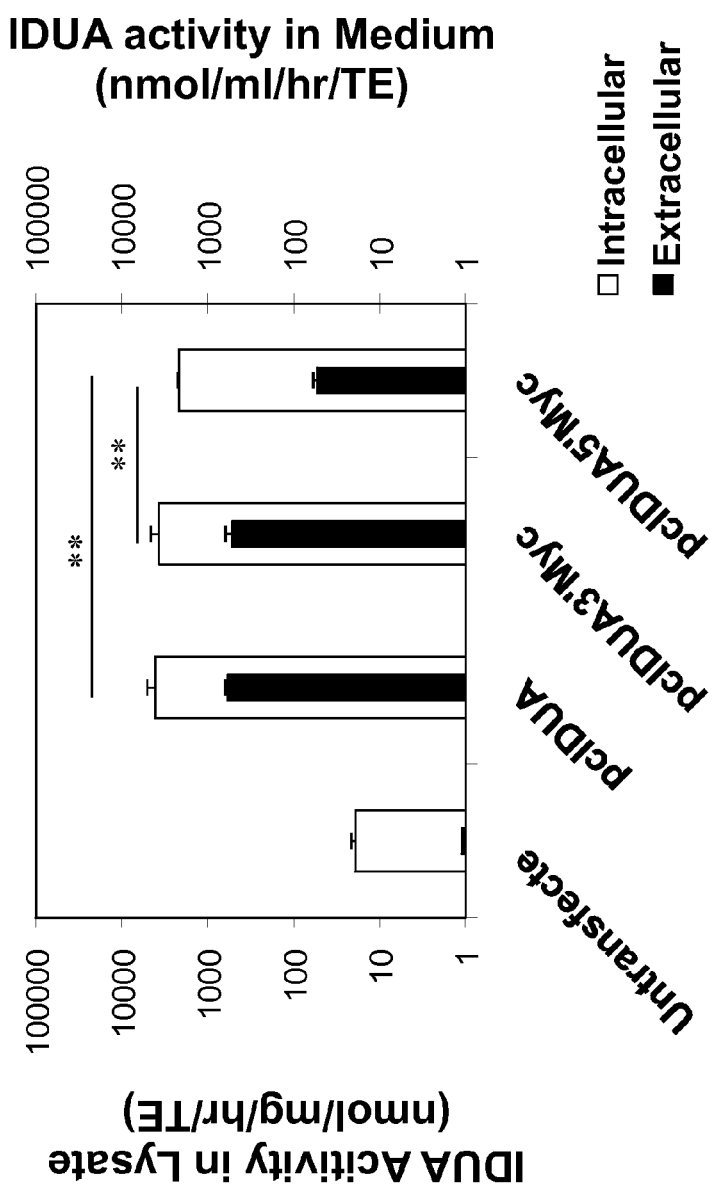
FIG. 1 depicts a bar chart illustrating the catalytic function of modified α-L-iduronidase (IDUA)-Myc fusion proteins. Human HEK293 cells were harvested 3 days after co-transfection of plasmidscontaining either the IDUA or a green fluorescent protein (GFP) sequence, after a 24-hour medium collection, and protein concentration was determined by Coomasie blue dye-binding assay. All activities were normalized by transfection efficiencies (TEs) determined using fluorescence-activated cell sorting (FACS) analysis for GFP+ cells (62-70%). Data were derived from two experiments in duplicate wells. **, $p<0.01$ by Student T-Test.

After confirmation of the modified IDUA by sequencing, the IDUA5'Myc, IDUA3'Myc, or unmodified human IDUA were cloned into plasmid pcDNA3.1 (with CMV promoter) and evaluated for expression in human HEK293 cells (FIG. 1).

The IDUA catalytic activity was determined with a fluorometric enzyme assay, as previously described with modifications (Wang, D. et al. *J. Gene Med.* 10:249-59 (2008)). Human HEK293 cells were harvested 3 days after co-transfection of the IDUA-containing plasmids, which also contained a green fluorescent protein (GFP) sequence, after a 24-hour medium collection. Cell pellets were homogenized in distilled water using an Ultrasonic Processor (GE, Fairfield, Conn.). Aliquots of cleared lysate, plasma or culture medium were incubated with 2.5 mM fluorogenic substrate and 4-methylumbelliferyl (4MU) α-L-idopyranosiduronic acid sodium salt (Toronto Research Chemicals, North York, Ontario, Canada), then analyzed with an emission wavelength of 450 nm and an excitation wavelength of 365 nm using a SpectraMax M5 Fluorometer (MDS Analytical Technologies, Sunnyvale, Calif.). All samples were assayed in duplicate reactions, and each reaction was quantified in duplicate wells. Protein concentration was measured by Coomassie blue dye-binding assay (BioRad, Hercules, Calif.). One unit (U) of enzyme activity was defined as the release of 1 nmol of 4MU in a 1-hr reaction at 37° C. The intracellular IDUA specific activity was calculated as U/mg protein, and extracellular IDUA activity as U/ml medium or plasma.

The addition of the myc-tag at the C-terminus (IDUA3'Myc), but not at the N-terminus (IDUA5'Myc), had no effect on either IDUA catalytic function or its discharge trafficking to the extracellular space (FIG. 1). No significant difference was detected between IDUA and IDUA3'Myc for introducing high enzyme activities in either the cell lysate (~200-fold of untransfected controls) or the culture medium (over 800-fold). In contrast, IDUA5'Myc was associated with a 48% reduction in intracellular IDUA activity and a more than 85% reduction in enzyme release into the medium. Thus, the addition of the Myc-tag at the C-terminus of IDUA did not appear to affect normal IDUA catalytic function and its discharge trafficking.

Characterization of the Released Form of IDUA-Myc. The released form(s) of IDUA were then evaluated to determine whether they still contained functioning Myc-tag (without removal by proteolytic process). Medium preconditioned by a 24-hour culture of HEK293 cells over-expressing natural or Myc-tagged IDUA was normalized to 200 nmol/hr/ml, followed by immunoprecipitation with beads coated with monoclonal antibody against Myc-tag or IgG control.

Figure 2:
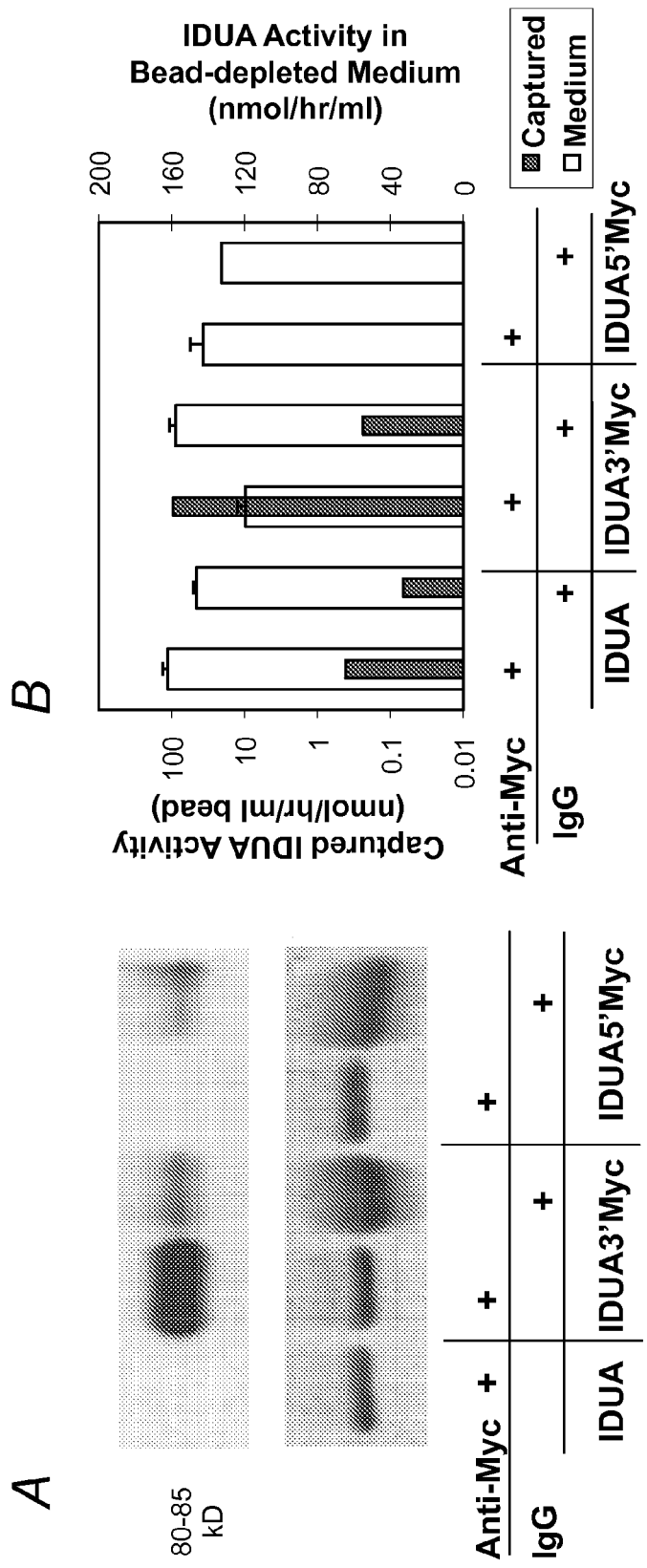
FIGS. 2A-B depict the binding ability of released Myg-tagged IDUA.

Western blot analysis showed that anti-Myc-antibody recognized a single peptide with an apparent molecular weight of 80-90 kD in medium derived from pcIDUA3'Myc transfected cells but not in those from pcIDUA5'Myc or pcIDUA, meaning that the released form of IDUA3'Myc still carried the tag sequence (FIG. 2A). This is similar to the molecular weight of normal unprocessed IDUA protein found in medium of IDUA-overexpressing human fibroblasts. Moreover, immunoprecipitated IDUA3'Myc protein was still catalytically active (>400 fold over IgG controls) while remaining captured, i.e. with epitope-binding by anti-myc immune-beads (FIG. 2B). These data indicate that the released IDUA from pcIDUA3'Myc transfected cells still carried the Myc epitope and that this modified protein remains bi-functionally active for Myc binding and for IDUA catalytic activity.

Receptor-mediated uptake. The cation-independent mannose-6-phosphate receptor (M6PR) system plays an important role in intracellular and intercellular trafficking of lysosomal enzymes, as the natural uptake of wild-type IDUA enzyme is mediated by M6PR and endocytosed into lysosomes/endosomes. Murine 3T3 cells were exposed for 2 hours to medium preconditioned by 24-hour culture of HEK293 cells overexpressing IDUA or IDUA3'Myc in the presence of various concentrations of mannose 6-phosphate (M6P) inhibitor and evaluated.

Figure 3:
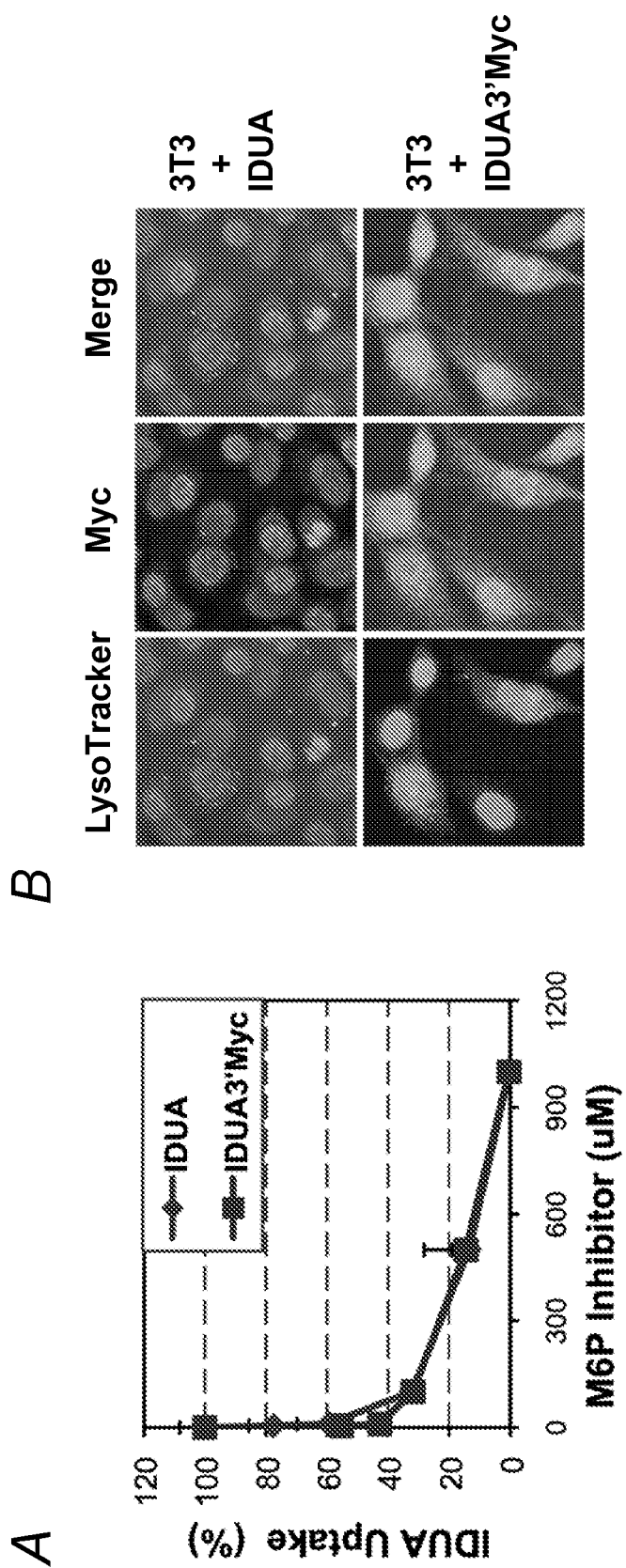
FIGS. 3A-B depict mannose-6-phosphate (M6P) uptake of IDUA-Myc fusion proteins.

A competitive uptake assay was performed to determine if the endogenous M6PR-mediated lysosomal targeting uptake pathway remains intact in fusion IDUA3'Myc with the addition of C-terminus Myc epitope (FIG. 3A) and by immunostaining analysis with co-localization of internalized IDUA3'Myc in the lysosome compartment (FIG. 3B). When supplying the same amount of active enzyme in medium, similar uptake activities were obtained in 3T3 cells among all three IDUAs. Moreover, the uptake process of fusion IDUA was inhibited by increasing the amount of M6P competitor, indicating that this uptake is mediated by MPR-dependent specific endocytosis. These results demonstrate that fusion IDUA3'Myc produced by "donor" cells can be endocytosed in the same manner as wild-type IDUA protein.

These data collectively indicate that the fusion IDUA with Myc epitope at C-terminus not only retained IDUA catalytic activity, lysosomal enzyme trafficking, and endogenous MPR-mediated uptake, but also acquired an additional epitope-binding ability in released IDUA, suggesting that the C-terminus of IDUA is suitable for ligand insertion in the construction of a fusion protein. Accordingly, it was concluded that this engineered IDUA protein could be used as a model protein to study added receptor-binding function without jeopardizing its natural functionalities.

Example 2

Design and Construction of a Plasmid for Expression of a Fusion Protein Containing a Binding Domain from Apolipoprotein E To select and identify an effective sequence of the LDLRf receptor-binding domain (Rb) of apolipoprotein E (apoE), a set of pcDNA3.1-based plasmids was constructed. The plasmids, which co-express neomycin-resistant gene (NeoR), were modified to include the IDUA protein modified with a Myc tag at the C-terminus and a binding sequence of apoE for the LDLR family. As discussed in Example 1, in preliminary data, it was demonstrated that the C-terminus of IDUA can be suitable for modification and that IDUA3'Myc retains normal biological function, enzyme trafficking, and release-uptake pathway. In addition, it was also demonstrated that the binding of the Myc-tag epitope could provide a marker for the detection of fusion proteins by molecular assay (FIGS. 2A-B) and by immunoprecipitation assay.

The base plasmid (pcIDUA3'Myc, also named as pcIDUAm for short) was engineered to include ClaI and XhoI restriction enzyme recognition sites downstream of the Myc-tag, as the backbone for in-frame insertion of Rb candidate sequences. In addition, an HpaI restriction enzyme recognition site was included in-frame upstream of Myc-tag as an alternative cloning site and for removal of Myc-tag for future clinical application.

Several studies on apoE have identified the extended putative receptor-binding domain as being in the vicinity of amino acid residues 130-150 of the mature apoE protein as made by annealing PCT cloning (as opposed to the native peptide precursor sequence) for the binding of apoE to the LDLR family. Synthetic peptides derived from this region were found to bind LDL receptor-related proteins (e.g. LRP1) or to mediate uptake of liposomes into rat primary blood capillary endothelial cells (BCECs). In addition, tandem dimers of residues (141-150) and (141-155) of the mature apoE protein have been found to mimic aspects of apoE binding or its function in vitro, while their monomeric peptides fail to do so. However, since none of the LDLRf binding domain of apoE has been reported in a fusion protein setting, determination of Rb sequences for successful "piggybacking" of a fusion protein across the BBB must rely on screening of multiple peptide sequences.

Based on available literature and consideration of dimeric effects, seven (7) candidates from the apoE receptor-binding region, which includes 4 tandem dimer candidates as well as one peptide candidate from the binding domain of apoB (3371-3409), were included for study. Table 3 provides the sequences of each candidate.

TABLE 3

Rb candidate sequences

| Candidate | Nucleic Acid Sequence* | Corresponding apoE Residues | Nucleic Acid SEQ ID NO. |
|---|---|---|---|
| "e1" | 5'-CGATctgcgcaagctgcgtaagcggctcctcctgcgcaagctgcgtaagcggctcctcC-3' (sense) | hApoE (141-149) x 2 (LRKLRKRLLLRKLRKRLL) SEQ ID NO: 14 | 1 |
| | 5'-TCGAGgaggagccgcttacgcagcttgcgcaggaggagccgcttacgc agcttgcgcagAT-3' (antisense) | | 2 |
| "e2" | 5'-CGATctgcgcaagctgcgtaagcggctcctccgcgatgccgatgacctgctgcgcaagct gcgtaagcggctcctccgcgatgccgatgacctgC-3' (sense) | hApoE (141-155) x 2 (LRKLRKRLLRDADDLLRKLR-KRLLRDADDL) SEQ ID NO: 15 | 3 |
| | 5'-TCGAGcaggtcatcggcatcgcggaggagccgcttacgcagcttgcgcagcagg tcatcggcatcgcggaggagccgcttacgcagcttgcgcagAT-3' (antisense) | | 4 |
| "e3" | 5'-CGATctgcgggtgcgcctcgcctcccacctgcgcaagctgcgtaagcggctcctcC-3' (sense) | hApoE (133-149) (LRVRLASHLRKLRKRLL) SEQ ID NO: 16 | 5 |
| | 5'-TCGAGgaggagccgcttacgcagcttgcgcaggtgggaggcgaggcgcacccgcagAT-3' (antisense) | | 6 |
| "e4" | 5'-CGATaccgaggagctgcgggtgcgcctcgcctcccacctgcgcaagctgcgtaagcgg ctcctcC-3' (sense) | hApoE (130-149) (TEELRVRLASHLRKLRKRLL) SEQ ID NO: 17 | 7 |
| | 5'-TCGAGgaggagccgcttacgcagcttgcgcaggtgggaggcgaggcgcacccgcagctcct cggtAT-3' (antisense) | | 8 |

TABLE 3-continued

Rb candidate sequences

| Candidate | Nucleic Acid Sequence* | Corresponding apoE Residues | Nucleic Acid SEQ ID NO. |
|---|---|---|---|
| "e5" | 5'-CGATctgcgggtgcgcctcgcctcccacctgcgcaagctgcgtaagcggctcctc ctgcgggtgcgcctcgcctcccacctgcgcaagctgcgtaagcggctcctcC-3' (sense) | hApoE (133-149) x 2 (LRVRLASHLRKLRKRLL-LRVRLASHLRKLRKRLL) SEQ ID NO: 18 | 9 |
| | 5'-TCGAGgaggagccgcttacgcagcttgcgcaggtgggaggcgaggcgcaccgcag gaggagccgcttacgcagcttgcgcaggtgggaggcgaggcgcaccgcagAT-3' (antisense) | | 10 |
| "e6" | 5'CGATaccgaggagctgcgggtgcgcctcgcctcccacctgcgcaagctgcgtaagcggctcctc accgaggagctgcgggtgcgcctcgcctcccacctgcgcaagctgcgtaagcggctcctcC-3' (sense) | hApoE (130-149) x 2 (TEELRVRLASHLRKLRKRLL-TEELRVRLASHLRKLRKRLL) SEQ ID NO: 19 | 11 |
| | 5'TCGAGgaggagccgcttacgcagcttgcgcaggtgggaggcgaggcgcaccgcagctcct cggtgaggagccgcttacgcagcttgcgcaggtgggaggcgaggcgcaccgcagctcctcggtAT-3' (antisense) | | 12 |
| "e7" | 5'CGATgctctgtctctgagcaacaaatttgtggagggtagtcataacagtactgtgagcttaac cacgaaaaatatggaagtgtcagtggcaaaaaccacaaaaccggaaattccaattttgC-3' | hApoB (3371-3409) (ALSLSNKFVEGSHNSTVSLT-TKNMEVSVATTTKAQIPIL) SEQ ID NO: 20 | 13 |

*The nucleotides in capital letters are not associated with "corresponding residues" but are related to the cloning strategy to make the cDNA of corresponding fusion proteins.

The seven Rb-IDUA fusion protein candidates were constructed at the C-terminus of IDUA3'Myc using a cloning strategy for inserting synthesized sense and antisense oligonucleotide sequences of Rb candidate binding regions into the XhoI site previously engineered into the IDUA-Myc sequence of the pcIDUAm plasmid (FIG. 4). An FspI restriction site is located in all Rb monomers and assisted in screening for desired colonies. Constructs were confirmed by sequencing across cloning junctions and named as pcIDUAmRb candidates.

Example 3

Evaluation of Expression and Release of Rb-IDUA

As a first step toward screening for the optimal Rb-IDUA fusion protein, murine 3T3 cell-based Rb-IDUA-overexpressing cell lines were established. Cells were co-transfected with pcIDUAmRb and pEF1a-GFP using TransIT 293 reagent. Two days later, an aliquot of cells was analyzed by FACS for GFP % to monitor general transfection efficiency (preferring under 20%) of each mixture of plasmids. Another aliquot was subcultured under G418 selection (0.4 mg/ml) at an appropriate ratio to keep similar numbers of transfectants among all pcIDUAmRb constructs. This was conducted to prevent gene expression in selected cell lines from being affected by having too few numbers of transductants (chromatin effect) or too high a transfection frequency (likely to have more cells containing >1 copy).

The intracellular Rb-IDUA expression was determined in each Rb-IDUA protein-producing cell line for catalytic activity in the cell lysate by IDUA enzyme assay, as previously described (Pan, D. et al. 2000. *Gene Ther.* 7:1875-1883, which is incorporated herein by reference in its entirety) (FIG. 5A). In addition, the following analyses were performed to compare extracellular Rb-IDUA in 24-hr preconditioned medium: i) catalytic activity in medium (FIG. 5A); ii) immunoprecipitation using anti-Myc coated immuno-beads, followed by Western blot analysis to confirm the existence of Myc-epitope in released form of Rb-IDUA (FIG. 5B), and iii) enzyme analysis for captured activity (FIG. 6).

Immunoprecipitation was performed by preconditioning medium (500 µl) by 24-hour culture of HEK293-based cells that stably overexpressed different Rb-IDUA, and incubating with protein A/G beads (50 µl, Invitrogen) pre-coated with mouse anti-c-Myc monoclonal antibody (5 µl, Santa Cruz) overnight at 4° C. 3T3 cells overexpressing unmodified IDUA were used controls in these studies.

IDUA catalytic activities were determined in cell lysates or 24-hour precondition medium ($10^6$ cells/3 ml) from different 3T3 cell-based fusion IDUA-overexpressing cell lines (FIG. 5A). Stable, IDUA-expressing cell lines were obtained by co-transfecting cells with two plasmids expressing either fusion IDUA or eGFP from a CMV promoter (with transfection frequency of 15-30%) and subsequent selection of transfectants by G418. Western blot analysis was performed on Myc-tagged fusion IDUA in medium (FIG. 5B). The rabbit anti-Myc polyclonal antibody was utilized to each lane loaded with 50 µl 24-hr precondition medium; the culture medium contained 10% fetal bovine serum.

All 7 IDUA fusion candidates were found to be expressed and released into the extracellular space (FIG. 5A). The released forms of IDUA fusion proteins still contained functioning myc-tag without proteolytic removal, a process known for all lysosomal enzymes (FIG. 5B). The released forms of all IDUA fusion candidates remained catalytically active while being captured by immunoprecipitation using anti-myc antibody (FIG. 6), thereby confirming the presence of Rb-insertion and the preservation of IDUA function.

Example 4

In Vitro Receptor-Mediated Uptake of Rb-IDUA

The LRP 1 receptor-specific uptake pathway was evaluated by generating LRP1 overexpressing cell lines based on $CHO^{LDLRneg}$ (Sege, R. et al. *Nature* 307:742-5 (1984)) or $MEF^{LRP1neg}$ cells. The $CHO^{LDLRneg}$ cell line was provided by Massachusetts Institute of Technology (Cambridge, Mass.), and $MEF^{LRP1neg}$ (PEA13) was obtained from ATCC (Manassas, Va.). The cell lines that over-express various IDUA fusion proteins or LRP1 were generated by transient co-transfection of pcDNA3.1-IDUA-Rb or pcDNA/Zeo-LRP1 with an eGFP-expressing plasmid (pEMiG) (Worsham, D. et al. *Mol. Ther.* 14:514-24 (2006)) to monitor transfection efficiency (45-65%). Cells were then subjected to G418 (0.45 mg/ml) (Invitrogen) or Zeocin™ (250-400 µg/ml) selection for stable transductants. Cells were routinely cultured in Dulbecco's Modified Eagle's Medium or RPMI 1640 medium (LifeTechnologies, Carlsbad, Calif.) with 10% Hyclone fetal bovine serum (FBS) (Thermo Fisher Scientific, Waltham, Mass.), 2 mM glutamine, and antibiotics. All cells were maintained at 37° C. in a humidified atmosphere containing 5% $CO_2$ and were routinely tested to verify the absence of *Mycoplasma* infection After establishment, the cell lines of either knock-down or over-expressing LRP1 (expressed in BCEC and brain tissues) were verified by Western blot analysis (FIG. 7). These cells allowed the evaluation of the uptake of candidate Rb-IDUA fusion protein with enhanced sensitivity mediated by specific LDLR family members.

To determine if any of the Rb candidates introduces an "adapted" LRP 1-mediated internalization pathway, an uptake-inhibition study was conducted by exposing $CHO^{LD-LRneg}$-LRP1 cells with medium containing each of the Rb-IDUA fusion proteins in the absence or presence of RAP inhibitor. To evaluate enzyme uptake mediated by specific receptor pathways, cells ($2\times10^5$/well) were seeded in 24-well plates. One day later, cells were incubated for 3 hours at 37° C. with 5% $CO_2$ with medium containing same activity levels of different IDUA candidates. To inhibit receptor-mediated uptake, 1 mM M6P (Sigma) or 5 µg/ml of RAP was added 30 minutes prior to and during the uptake incubation, in parallel with untreated wells, with enzyme-containing medium. Each experiment was performed in duplicate wells. Media conditioned by 24-hour culture of each of the 3T3-Rb-IDUA cell lines were employed as enzyme source, together with that of 3T3-IDUA3'Myc as the control (approximately 800-fold higher than 3T3 controls) for uptake screening using $CHO^{LDLRneg}$-LRP1 cells.

For this transcytosis analysis, the upper chambers of 6-well transwells (0.4 µM, BD Biosciences) were pre-coated with Type I Collagen (50 µg/ml) (Santa Cruz Biotechnology, Santa Cruz, Calif.). Bovine brain microvascular endothelial cells (CRL-12414, ATCC) were cultured in the collagen-coated upper chamber of transwells for two days, followed by exposure to a medium containing IDUA3' myc or IDUA fusion candidates at 4° C. for 30 minutes in the presence or absence of RAP (5 µg/ml) competitor. After rinse with PBS for three times, the cells on the transwells were transferred to a new chamber and cultured at 37° C. with fresh culture medium for 3 hours. Media in lower chambers were collected (300 µl) periodically at different time points during incubation. Modified IDUA protein was captured by immuno-precipitation (overnight at 4° C.) using anti-myc-antibody coated Protein A/G beads (30 µl) and quantified by IDUA enzyme assay, as described above. To control for varying leakage of the BMEC layer among individual experiments, every experiment included IDUA3' myc in parallel with all three selected Rb-IDUA proteins, and all transcytosis assays involving RAP were performed in parallel with untreated assays.

The uptake of three candidates (IDUAe1, IDUAe2, and IDUAe5) was found to be only partially blocked by M6P for the endogenous MPR pathway and significantly reduced by RAP for the LRP1 pathway (FIG. 8A). The competitive inhibition for endogenous M6PR-mediated uptake was also assessed in these cell lines by dose-dependent inhibition experiments with the competitive inhibitor M6P, after culturing cells for two hours with similar amounts of IDUA3'Myc (~500 nmol/hr/min) in the presence or absence of increasing amounts of M6P inhibitor (FIG. 9).

When treated with comparable levels of activities, candidate IDUAe1 resulted in higher uptake compared with unmodified IDUA (FIG. 8B). The results showed that, in comparison to IDUA3'Myc, the uptake of IDUAe1, IDUAe2, and IDUAe5 was only partially inhibited (less than 50%) by M6P but was significantly reduced by RAP. To evaluate these three candidates during one cycle of LRP 1-mediated receptor binding and internalization process, a pause-chase-like analysis was performed by exposing $CHO^{LDLRneg}$-LRP1 cells to these three candidates with the same IDUA activity for 20 minutes at 4° C. to allow maximum receptor binding, followed by multiple wash steps to remove the fusion IDUA and subsequent culture in fresh medium at 37° C. for 1 hour to allow protein internalization (FIG. 8B).

A highly efficient (comparable to M6PR-mediated) LRP 1-mediated internalization of IDUAe1 was evident by a 2-fold higher intracellular enzyme level that could be partially blocked (~50%) upon RAP inhibition. A noticeable observation was that the uptake of IDUAe2 was partially inhibited by the combination of RAP (⅓) and M6P (less than ¼), suggesting the involvement of an alternative receptor from the LDLR superfamily. The specific binding of IDUAe1 and IDUAe2 to LRP1 was further supported by an inhibitory binding assay using immunoprecipitation with anti-LRP1 antibody using cells either lacking or overexpressing the LRP1 receptor (FIG. 8C); these results indicate specific binding of LRP1 and IDUAe1 and IDUAe2. Cells were exposed at 4° C. for 20 min to IDUA fusion proteins with the same IDUA activity (500 nmol/ml) in the presence or absence of RAP inhibitor.

Immunoprecipitation was performed by exposing MEF-based cells to IDUA fusion proteins with the same IDUA activity (500 nmol/ml) at 4° C. for 20 min, followed by three rinses with PBS, then immunoprecipitation was performed with cell lysates using protein beads that were pre-coated with rabbit anti-LRP1 polyclonal antibody (1:200, 0.4 mg/ml), as previously described (Basford, J. et al. *J. Biol. Chem.* 286:13079-87 (2011)). The inhibitory binding was conducted in parallel with untreated wells by the addition of 5 µg/ml of recombinant RAP (Williams, S. et al. *J. Biol. Chem.* 267:9035-40 (1992)) 30 minutes before and during the incubation of IDUA fusion proteins. Post-precipitation, beads were washed three times, and IDUA enzyme assay was then performed with the washed immune-beads.

Both IDUAe1 and IDUAe2 were found to introduce significantly higher LRP1 binding, which was blocked by RAP, in LRP1-overexpressing cells than in LRP 1-null MEF cells.

The results from this initial screening of receptor-binding and internalization capabilities led to the selection of fusion protein candidates IDUAe1, IDUAe2, and IDUAe5 for further evaluation. Their ability to mediate transendothelial transport was assessed using an in vitro BBB model employing bovine microvascular endothelial cells (BMECs) cultured in the upper chamber of collagen-coated transwells (0.4 µm). Two days later, they were exposed to conditional medium containing IDUA3' myc or fusion IDUA for 30 minutes at 4° C. After thorough wash, the cells on the transwells were transferred to a new chamber and cultured at 37° C. with fresh culture medium for 3 hr, in the presence or absence of RAP competitor. IDUA protein in the lower chambers were captured at different time points by immunoprecipitation using Myc-antibody and quantified by IDUA enzyme assay (FIG. 10A).

The non-transcytotic leakage of the BMEC layer was monitored by parallel experiments using IDUA3'Myc control at the same enzymatic levels. Utilizing a modified pause-chase assay, transcytosis of IDUAe1 and IDUAe2, but not IDUAe5, was indicated by a steady increase of captured enzymatic levels found in the lower chambers (up to 3.6-fold over plateau levels of IDUA3'Myc) after the removal of fusion proteins from the upper chambers. This elevation could be blocked by RAP inhibitor for IDUAe1 but less so for IDUAe2, indicating that the elevated transport process of IDUAe1 was mediated by LRP1.

The functional integrity of fusion Rb-IDUAs and their ability to achieve metabolic cross-correction in patient cells was determined by in situ immunostaining using a fluorescent dye that can be endocytosed into lysosomes using enzyme-deficient fibroblasts from patients with MPS I, as described previously ($F_{MPS}$) (Pan, D. et al. 2000. *Gene Ther.* 7:1875-1883). Primary fibroblasts from an MPS I patient were purchased from Coriell Cell Repositories (Camden, NJ). Cells that had been grown on poly-L-lysine (Sigma)-coated cover slides in the lower chambers of transwells (0.4µM) were co-cultured for 24 hours with HEK293-based cell lines that overexpressed IDUA or IDUA fusion candidates. Fibroblasts on slides were washed in PBS and incubated with 75 nM LysoTracker Red (Invitrogen) for 1 hour at 37 ° C. The slides were then fixed with 4% paraformaldehyde and mounted using VECTASHIELD mounting medium with DAPI (Vector Laboratories, Burlingame, CA), and fluorescence microscopy was conducted using a DMI6000 B microscope system (Leica Microsystems, Wetzlar, Germany).

Representative photomicrographs of lysosomal morphology were taken following immunofluorescent staining with LysoTracker for lysosomes and DAPI for nuclei (FIG. 10B). In contrast to untreated primary fibroblasts from a MPS I patient (FMPS) that exhibited excessive abundance of lysosomes and the abnormal lysosomal morphology, the majority of FMPS cells exposed to fusion Rb-IDUA exhibited a normalized lysosomal pattern. Thus, the released forms of IDUAe1 and IDUAe2 are fully functional and are suitable for uptake by cells via M6PR- and LRP1-mediated endocytosis. These results demonstrate that IDUAe1 and IDUAe2 can be used for cross-correction of phenotypic defects in cells from MPS I patients.

Example 5

In Vivo Evaluation of Rb-IDUA

After in vitro screening using cell lines and the BBB culture model, in vivo evaluation was initiated for BBB transport. Fusion protein candidates IDUAe1 and IDUAe2 were evaluated for their potential for in vivo brain delivery in MPS mice.

Hydrodynamic tail vein injection for transient high Rb-IDUA in circulation. A simple and efficient non-viral gene delivery approach via hydrodynamic tail-vein (HTV) injection of naked plasmid DNA, which has been proven to introduce high transgene expression in the liver of small rodents, was employed for these experiments. It is well-tolerated in mice and rats with transient elevation of plasma alanine aminotransferase, and peak expression levels are observed predominantly in hepatocytes (>90%) at 2-5 days post injection.

The convenience and effectiveness of in vivo hydrodynamic gene delivery have provided a unique platform to evaluate biology, physiology, and immune responses of gene therapy approaches in vivo. The feasibility of nonviral gene transfer by the hydrodynamic method has been demonstrated recently in large animals for the efficient production of secreted protein in pigs with the insertion of a catheter in the hepatic vein and the occlusion of the portal vein and the hepatic artery. Therefore, liver-targeted HTV injection will provide a suitable system for in vivo screening of Rb-IDUA, as well as the gene transfer approach.

The expression of IDUA fusion candidates in the liver was further restricted by utilizing a liver-specific hybrid promoter to eliminate any fusion protein production in the CNS. MPS I mice (B6.129-idua$^{tm1Clk}$) and wild type C57/B16 mice were obtained from the Jackson Laboratory (Bar Harbor, Me.). After in-house backcrossing with C57/B16 for more than 9 generations, experimental groups were generated in a pathogen-free facility (with micro-isolator) at Cincinnati Children's Research Foundation (CCRF, Cincinnati, Ohio) and genotyped, as previously described (Pan, D. et al. *Brain Res.* 1188:241-53 (2008)).

For transient in vivo gene transfer by HTV injection, a total of 50 µg plasmid DN, that expressed one of the selected IDUA fusion proteins from a liver-specific promoter was injected rapidly into MPS I mice (7-8 weeks old) under restraint by intravenous administration via tail-vein in a volume of saline equivalent to 10% of the body mass of the mouse (n=4 to 8). The total volume was delivered within 5-8 seconds using a 26-gauge insulin syringe-needle. Injected mice were monitored for recovery to normal activity within 5 minutes post-injection. Blood samples were collected at various time points by tail bleed and analyzed to monitor plasma IDUA activities. Robust (20- to 500-fold of heterozygous carrier levels) and continuous (up to 3 days) protein production was achieved in the circulation of all injected enzyme-deficient mice (FIG. 11), thus presenting a practical time-window for in vivo evaluation of brain delivery across the BBB.

To determine whether modified IDUA could be effectively produced in circulation in vivo, plasmids expressing IDUAmyc, IDUAel, or IDUAe2 from a hepatic-specific promoter were injected via hydrodynamic procedure into 6-8 week old mice models for MPS I (FIG. 12A). Two days after HTV injection, mice were anesthezed by intraperitoneal injection with an overdose of sodium Nembutal (Abbott Laboratories, Abbott Park, IL), followed by transcardial perfusion via aorta with cold saline to remove blood from the vasculature. The success of this procedure was confirmed by a loss of color in the liver and the blood vessels that flank the midline of the rib cage. Brain capillary depletion was carried out, as previously described (El-Amouri, S. et al. 2013.

Molecular Biotechnology 53(1):63-73). Freshly removed mouse brains were homogenized on ice with 10 strokes in capillary depletion buffer, followed by dextran-gradient centrifugation (16%) at 5400xg for 15 minutes at 4° C. The supernatants containing brain tissues and the pellets containing the capillaries were carefully separated, washed three times with PBS, and followed by IDUA enzyme analysis.

Elevated IDUA activities (from un-detectable to 24-100 fold higher than heterozygous levels) were found in plasma of all injected mice 2 days after injection. Moreover, the in vivo secreted Myc-IDUA was captured by immune-beads coated with anti-Myc antibody and remained catalytically active while bound by antibody. These data illustrate the feasibility of achieving in vivo a robust and relatively stable delivery of protein in circulation by hydrodynamic tail injection of a mouse model for disease. This approach accordingly provides a practical window for in vivo evaluation of Rb-IDUA delivery across the BBB.

Quantitative evaluation of Rb-IDUA Transport in the central nervous system. To distinguish the fraction of transcytosed Rb-IDUA that has entered brain extracellular space or brain cells from that associated with the BBB-forming endothelial cells, brain capillary depletion was performed, as previously described (Urayama, A. et al. *Proc Natl Acad Sci U.S.A.* 101:12658-12663 (2004), which is incorporated herein by reference in its entirety). Two-days after HTV injection of plasmids expressing fusion IDUA from a liver-specific hybrid promoter into MPS I mice, whole brains were collected from well-perfused animals and emulsified in a glass homogenizer at 4° C. in a physiological buffer. An aliquot of brain homogenate was stored at −20° C. for later Western blot analysis. Dextran solution was added to the homogenate and followed by centrifugation at 5,400×g in a cold environment to separate the vascular component from the rest of brain. The catalytic activity of IDUA was measured using a standard fluorometry enzyme assay in capillary-depleted parenchyma and microvessel fractions (FIG. 12A) and normalized by protein concentration determined using Coomasie blue dye-binding assay (BioRad).

In contrast to the lower-than-control enzyme activities (~⅓ of IDUA3'Myc) found in the plasma, the IDUA enzyme activities in brain tissues and capillaries of both IDUAe1- and IDUAe2-injected MPS mice were significantly higher (10- to 30-fold) than those of IDUA3'Myc control groups, which exhibited the highest plasma IDUA activities. These brain IDUA levels, equivalent to 3-5% of normal levels, are significant considering that minimum amounts of enzyme (e.g., 1-5% of normal serum enzyme levels) have been associated with clinical benefits in MPS I patients after successful bone marrow transplantation.

Identity of brain cells taking up Rb-IDUA. To identify which types of brain cells accumulate Rb-IDUA, frozen brain sections from perfused animals were analyzed by immunohistochemistry with anti-Myc for Myc-tagged fusion IDUA and cell-specific markers. A portion (the forebrain cortical region) of freshly removed brain from perfused animal was postfixed in 4% paraformaldehyde, followed by incubation overnight at 4° C. in 4% paraformaldehyde containing 30% sucrose. Frozen sections (10 μm) were obtained and permeabilized with PBS containing 0.1% Triton X-100 and treated with blocking solution (PBS containing 5% horse serum and 0.1% Triton X-100). Sections were then incubated overnight at 4° C. with the primary antibody: sheep anti-hIDUA (1:100, R&D Systems, Minneapolis, Minn.), rabbit anti-NeuN (1:200, EnCor Biotechnology, Gainesville, Fla.) for neuronal cells, rat anti-mouse CD31 (1:200, BD Pharmingen, Franklin Lakes, N.J.) for BBB-forming endothelial cells, and rabbit anti-GFAP (1:250, Abcam, Cambridge, United Kingdom) as a marker for astrocytes. Slices were washed three times with PBS and incubated with a secondary antibody of the appropriate species, including Alexa 488 donkey anti-sheep (1:500, Invitrogen), Alexa 568 goat anti-rabbit (1:500) and Alexa 568 goat anti-rat (1:500). Slices were mounted with Vectashield mounting medium containing 4,6-diamidino-2-phenylindole (DAPI; Vector Laboratories) counterstain for nuclei and analyzed via immunofluorescent microscopy using a DMI6000 B microscope system.

These immunofluorescence studies demonstrated the presence of IDUAe1 or IDUAe2 positive cells primarily in non-endothelium perivascular cells, neurons, and less so in astrocytes of cerebra of injected mice (FIGS. 12B-D). The passage of both IDUAe1 and IDUAe2 across the BBB was visualized by IDUA positive staining in the abluminal side adjacent to BBB-forming capillary endothelia cells labeled by CD31 marker (FIG. 12B). Based on their bordering location by the endothelium, astrocyte end-feet and/or pericytes are indicated for uptake of the trans-luminal delivered IDUAe1 and IDUAe2. The delivery of liver-derived IDUAe1 and IDUAe2 into neurons was also demonstrated by co-localization of the IDUA protein with NeuN, a nuclear marker associated with the majority of neurons, throughout the brain. In contrast, lack of co-localization was found in IDUA3'Myc-treated brains (FIG. 12C). Cells that were stained positively for both IDUA and GFAP, a marker for astrocytes, in the forebrain of IDUA-knockout mice injected with IDUAe1 or IDUAe2 plasmids, but not with IDUA3'Myc controls, were also observed (FIG. 12D). These results demonstrate that the BBB-targeted Rb-IDUA can be delivered across BBB to non-endothelium perivascular cells, neurons, and astrocytes in the CNS.

The abnormal accumulation of glycosaminoglycans (GAGs) in all organs, which is a direct consequence of IDUA enzyme deficiency, is the metabolic basis for MPS I disease. In order to determine whether CNS delivery of Rb-IDUA is sufficient to reduce lysosomal storage in the diseased brain of MPS I mice, two to three aliquots of frozen brain samples were homogenized in a minimum volume of water (10% vol/weight). Similar amounts of brain samples (~1 mg of protein) were defatted by treatment with a chloroform:methanol (1:2) mixture and washed with 100% ethanol, followed by digestion with papain solution (in 100 mM sodium acetate buffer with pH 5.5 and containing 5 mM cysteine and 5 mM EDTA) (Sigma, St. Louis, Mo.). Samples were then treated with DNase (1U/μl) for 30 min at 37° C. Soluble GAG was quantified in duplicate reactions using 1,9-dimethylmethylene blue chloride dye, as previously described (Barbosa, I. et al. *Glycobiology* 13:647-53 (2003)) with modification. Absorbance of the color reaction was measured at 656 nm using a SpectraMax M2 microplate reader and compared with a standard curve generated with heparan sulfate standard solutions (Sigma). Protein concentration was measured using a BCA Protein Assay kit (Thermo Fisher Scientific). All GAG values were normalized to the amounts of total protein.

Brain GAG levels were assessed two days after HTV injection into MPS I mice (FIG. 12E). The GAG accumulation was found to be normalized in MPS mice treated with IDUAe1-expressing plasmid, suggesting brain metabolic correction in these animals. IDUAe2 only introduced GAG reduction to some extent even though similar levels of elevated enzyme activities were detected in the brains of both IDUAe1- and IDUAe2-treated MPS mice. The difference in sub-cellular localization of IDUAe1 and IDUAe2 dictated by less M6PR-mediated internalization of IDUAe2, as indicated previously by in vitro screening, therefore affects GAG normalization in CNS parenchyma. These data documented CNS delivery of liver-derived IDUAe1 to be more biologically efficacious, indicating strong therapeutic potential of CNS-targeted Rb-fusion protein.

Example 6

Construction of a Lentiviral Plasmid Construct for Targeted Delivery and Liver-Specific Expression of Rb-IDUA A system to deliver and express a nucleic acid sequence encoding Rb-IDUA in the liver is developed.

Continuously supraphysiological levels of IDUA enzyme were obtained in circulation during a 100-day observation in MPS I mice treated by $2 \times 10^7$ TU neonatal IV injection of a single dose of therapeutic lentiviral vector LV-PGK-IDUA with predominantly liver gene transfer (FIGS. 13A-C). In this case, the liver acted as a robust source of enzyme depot to produce and distribute high and prolonged levels of therapeutic agent systemically to other organs.

No detectable activity was found in any of the MPS I tissues 100 days after injection (FIG. 13A). The various levels of pathological correction in CNS were compared (FIG. 13B). Behavioral improvement was observed in a 6-arm water maze test after allowing mice two daily trials of 1-minute platform learning for nine days (FIG. 13C).

Accordingly, a non-replicating and self-inactivating (SIN) lentiviral vector is developed to deliver a nucleic acid sequence encoding an Rb-IDUA fusion protein to the liver or to hepatic tissue in vivo or in vitro. The vector includes a hepatic-specific promoter for liver tissue-specific expression of the fusion protein as described herein. It is found that a SIN lentiviral vector encoding Rb-IDUAe1 or Rb-IDUAe2 results in sustained liver tissue-specific expression of catalytically active IDUA that is able to transcytose across the BBB.

Example 7

Construction of a Lentiviral Plasmid Construct for Hematopoietic Stem Cell Expression of Rb-IDUA A system to administer a nucleic acid sequence encoding Rb-IDUA to hematopoietic stem cells (HSCs) is developed.

A non-replicating and self-inactivating (SIN) lentiviral vector is developed to deliver and integrate a nucleic acid sequence encoding an Rb-IDUA fusion protein into an HSC. The vector can include an HSC-specific promoter, such as, for example, an erythroid-specific hybrid IHK promoter, as previously described (Moreau-Gaudry, F. et al. 2001. *Blood* 98:2664-2672, which is incorporated herein by reference in its entirety) for expression of the fusion protein as described herein. It is found that administration of a SIN lentiviral vector encoding Rb-IDUAe1 or Rb-IDUAe2 results in sustained and HSC-specific expression of catalytically active IDUA. Upon administration of the transformed HSC to a subject, it is found that the HSC-expressed IDUA is able to transcytose across the BBB.

Example 8

Treatment of a Subject Having Mucopolysaccharidosis Type I by Administration of a Nucleic Acid Encoding Rb-IDUA A subject is diagnosed as having MPS I. The subject is administered a nucleic acid molecule encoding Rb-IDUA as herein disclosed that is operably linked to a tissue-specific or organ-specific promoter. Subsequently, the subject's tissue or organ expresses Rb-IDUA protein that is catalytically active and able to transcytose across the BBB, resulting in alleviation of symptoms associated with MPS I.

Example 9

Treatment of a Subject Having Mucopolysaccharidosis Type I by Administration of a Fusion Protein Containing Rb-IDUA A subject is diagnosed as having MPS I. The subject is administered a fusion protein containing Rb-IDUA. The circulating Rb-IDUA is able to transcytose across the BBB, resulting in alleviation of symptoms associated with MPS I.

Example 10

Treatment of a Subject Having Mucopolysaccharidosis Type I by Transplantation of Transformed Cells A subject is diagnosed as having MPS I. HSCs are transformed with a viral vector containing a nucleic acid molecule encoding Rb-IDUA fusion protein as described (Example 7) and selected for transformed cells. Clonal expansion of a successfully transformed cell is achieved, and the cells are transplanted into the subject's bone marrow. Once transplanted into the subject, the transformed cells are able to express and secrete Rb-IDUA, which is circulated in the subject's body and is able to transcytose across the BBB, resulting in alleviation of symptoms associated with MPS I.

All quantitative assays described above were performed in duplicate or triplicate from at least two individual experiments. Data are presented as mean±standard deviation (s.d.) unless specified. Comparisons between two groups were performed using two-tailed Student t-tests. P values of less than 0.05 were considered as statistical significance.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the numbers expressing quantities of ingredients, properties such as molecular weight, reaction conditions, and so forth, used to describe and claim certain embodiments of the application are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

What is claimed is:

1. A composition comprising a peptide sequence, the peptide sequence comprising (1) an oligomer of a receptor-binding region of apolipoprotein E (apoE) and (2) a protein, wherein
the oligomer of the receptor-binding region of apoE is
(b) SEQ ID No: 19;
the peptide sequence does not comprise SEQ ID NO:14;
the peptide sequence does not comprise SEQ ID NO:15;
the composition is suitable for crossing the blood brain barrier; and
the peptide sequence is expressed as a fusion protein.

2. A composition comprising a nucleic acid molecule, wherein the nucleic acid molecule comprises a sequence encoding a peptide sequence of claim 1.

3. A method of producing a genetically engineered cell line expressing the peptide sequence of claim 1, the method comprising:
identifying a cell line of interest to be transformed;
introducing a nucleic acid molecule into the genetic material of a cell from the cell line of interest, wherein the nucleic acid molecule encodes a fusion protein comprising the peptide sequence of claim 1;
selecting for a successfully transformed cell; and
cloning the transformed cell, wherein the genetically engineered cell expresses the protein of interest.

4. The composition of claim 1, wherein the peptide sequence is conjugated to an agent that mediates delivery to a target site.

5. The composition of claim 4, wherein the agent that mediates delivery to a target site comprises nanoparticles or liposomes.

6. A composition comprising a peptide sequence, the peptide sequence comprising (1) an oligomer of a receptor-binding region of apolipoprotein E (apoE) and (2) a protein, wherein
the oligomer of the receptor-binding region of apoE is
(b) SEQ ID No: 19;
the peptide sequence does not comprise SEQ ID NO:14;
the peptide sequence does not comprise SEQ ID NO:15;
the composition is suitable for crossing the blood brain barrier;
the composition is (1) suitable for treating a neurological disorder, disease, or symptom thereof, (2) suitable for treating a lysosomal storage disease, or (3) both; and
the peptide sequence is expressed as a fusion protein.

7. The composition of claim 6, wherein the peptide sequence is conjugated to an agent that mediates delivery to a target site.

\* \* \* \* \*

SEQUENCE LISTING

```
<160> NUMBER OF SEQ ID NOS: 21

<210> SEQ ID NO 1
<211> LENGTH: 59
<212> TYPE: DNA
<213> ORGANISM: Artificial Sequence
<220> FEATURE:
<223> OTHER INFORMATION: DNA sequence corresponding to potential
      receptor-binding region of Homo sapiens protein apolipoprotein E
      (ApoE); e1; sense

<400> SEQUENCE: 1
cgatctgcgc aagctgcgta agcggctcct cctgcgcaag ctgcgtaagc ggctcctcc      59

<210> SEQ ID NO 2
<211> LENGTH: 61
<212> TYPE: DNA
<213> ORGANISM: Artificial Sequence
<220> FEATURE:
<223> OTHER INFORMATION: DNA sequence corresponding to potential
      receptor-binding region of Homo sapiens protein apolipoprotein E
      (apoE); e1; antisense

<400> SEQUENCE: 2
tcgaggagga gccgcttacg cagcttgcgc aggaggagcc gcttacgcag cttgcgcaga    60
```

```
t                                                             61

<210> SEQ ID NO 3
<211> LENGTH: 95
<212> TYPE: DNA
<213> ORGANISM: Artificial Sequence
<220> FEATURE:
<223> OTHER INFORMATION: DNA sequence corresponding to potential
      receptor-binding region of Homo sapiens protein apolipoprotein E
      (apoE); e2; sense

<400> SEQUENCE: 3
cgatctgcgc aagctgcgta agcggctcct ccgcgatgcc gatgacctgc tgcgcaagct    60
gcgtaagcgg ctcctccgcg atgccgatga cctgc                              95

<210> SEQ ID NO 4
<211> LENGTH: 97
<212> TYPE: DNA
<213> ORGANISM: Artificial Sequence
<220> FEATURE:
<223> OTHER INFORMATION: DNA sequence corresponding to potential
      receptor-binding region of Homo sapiens protein apolipoprotein E
      (apoE); e2; antisense

<400> SEQUENCE: 4
tcgagcaggt catcggcatc gcggaggagc cgcttacgca gcttgcgcag caggtcatcg    60
gcatcgcgga ggagccgctt acgcagcttg cgcagat                            97

<210> SEQ ID NO 5
<211> LENGTH: 56
<212> TYPE: DNA
<213> ORGANISM: Artificial Sequence
<220> FEATURE:
<223> OTHER INFORMATION: DNA sequence corresponding to potential
      receptor-binding region of Homo sapiens protein apolipoprotein E
      (apoE); e3; sense

<400> SEQUENCE: 5
cgatctgcgg gtgcgcctcg cctcccacct gcgcaagctg cgtaagcggc tcctcc        56

<210> SEQ ID NO 6
<211> LENGTH: 58
<212> TYPE: DNA
<213> ORGANISM: Artificial Sequence
<220> FEATURE:
<223> OTHER INFORMATION: DNA sequence corresponding to potential
      receptor-binding region of Homo sapiens protein apolipoprotein E
      (apoE); e3; antisense

<400> SEQUENCE: 6
tcgaggagga gccgcttacg cagcttgcgc aggtgggagg cgaggcgcac ccgcagat      58

<210> SEQ ID NO 7
<211> LENGTH: 65
<212> TYPE: DNA
<213> ORGANISM: Artificial Sequence
<220> FEATURE:
<223> OTHER INFORMATION: DNA sequence corresponding to potential
      receptor-binding region of Homo sapiens protein apolipoprotein E
      (apoE); e4; sense

<400> SEQUENCE: 7
cgataccgag gagctgcggg tgcgcctcgc ctcccacctg cgcaagctgc gtaagcggct    60
cctcc                                                               65
```

<210> SEQ ID NO 8
<211> LENGTH: 67
<212> TYPE: DNA
<213> ORGANISM: Artificial Sequence
<220> FEATURE:
<223> OTHER INFORMATION: DNA sequence corresponding to potential
      receptor-binding region of Homo sapiens protein apolipoprotein E
      (apoE); e4; antisense

<400> SEQUENCE: 8
tcgaggagga gccgcttacg cagcttgcgc aggtgggagg cgaggcgcac ccgcagctcc    60
tcggtat                                                             67

<210> SEQ ID NO 9
<211> LENGTH: 107
<212> TYPE: DNA
<213> ORGANISM: Artificial Sequence
<220> FEATURE:
<223> OTHER INFORMATION: DNA sequence corresponding to potential
      receptor-binding region of Homo sapiens protein apolipoprotein E
      (apoE); e5; sense

<400> SEQUENCE: 9
cgatctgcgg gtgcgcctcg cctcccacct gcgcaagctg cgtaagcggc tcctcctgcg    60
ggtgcgcctc gcctcccacc tgcgcaagct gcgtaagcgg ctcctcc                 107

<210> SEQ ID NO 10
<211> LENGTH: 109
<212> TYPE: DNA
<213> ORGANISM: Artificial Sequence
<220> FEATURE:
<223> OTHER INFORMATION: DNA sequence corresponding to potential
      receptor-binding region of Homo sapiens protein apolipoprotein E
      (apoE); e5; antisense

<400> SEQUENCE: 10
tcgaggagga gccgcttacg cagcttgcgc aggtgggagg cgaggcgcac ccgcaggagg    60
agccgcttac gcagcttgcg caggtgggag gcgaggcgca cccgcagat              109

<210> SEQ ID NO 11
<211> LENGTH: 125
<212> TYPE: DNA
<213> ORGANISM: Artificial Sequence
<220> FEATURE:
<223> OTHER INFORMATION: DNA sequence corresponding to potential
      receptor-binding region of Homo sapiens protein apolipoprotein E
      (apoE); e6; sense

<400> SEQUENCE: 11
cgataccgag gagctgcggg tgcgcctcgc ctcccacctg cgcaagctgc gtaagcggct    60
cctcaccgag gagctgcggg tgcgcctcgc ctcccacctg cgcaagctgc gtaagcggct   120
cctcc                                                              125

<210> SEQ ID NO 12
<211> LENGTH: 127
<212> TYPE: DNA
<213> ORGANISM: Artificial Sequence
<220> FEATURE:
<223> OTHER INFORMATION: DNA sequence corresponding to potential
      receptor-binding region of Homo sapiens protein apolipoprotein E
      (apoE); e6; antisense

<400> SEQUENCE: 12
tcgaggagga gccgcttacg cagcttgcgc aggtgggagg cgaggcgcac ccgcagctcc    60

```
tcggtgagga gccgcttacg cagcttgcgc aggtgggagg cgaggcgcac ccgcagctcc    120
tcggtat                                                             127

<210> SEQ ID NO 13
<211> LENGTH: 122
<212> TYPE: DNA
<213> ORGANISM: Artificial Sequence
<220> FEATURE:
<223> OTHER INFORMATION: DNA sequence corresponding to potential
      receptor-binding region of Homo sapiens protein apolipoprotein E
      (apoB) - e7

<400> SEQUENCE: 13
cgatgctctg tctctgagca acaaatttgt ggagggtagt cataacagta ctgtgagctt    60
aaccacgaaa aatatggaag tgtcagtggc aaaaaccaca aaaccggaaa ttccaatttt   120
gc                                                                 122

<210> SEQ ID NO 14
<211> LENGTH: 18
<212> TYPE: PRT
<213> ORGANISM: Artificial Sequence
<220> FEATURE:
<223> OTHER INFORMATION: e1 - hApoE (141-149) x 2

<400> SEQUENCE: 14

Leu Arg Lys Leu Arg Lys Arg Leu Leu Leu Arg Lys Leu Arg Lys Arg
1               5                   10                  15

Leu Leu

<210> SEQ ID NO 15
<211> LENGTH: 30
<212> TYPE: PRT
<213> ORGANISM: Artificial Sequence
<220> FEATURE:
<223> OTHER INFORMATION: e2 - hApoE (141-155) x 2

<400> SEQUENCE: 15

Leu Arg Lys Leu Arg Lys Arg Leu Leu Arg Asp Ala Asp Asp Leu Leu
1               5                   10                  15

Arg Lys Leu Arg Lys Arg Leu Leu Arg Asp Ala Asp Asp Leu
            20                  25                  30

<210> SEQ ID NO 16
<211> LENGTH: 17
<212> TYPE: PRT
<213> ORGANISM: Artificial Sequence
<220> FEATURE:
<223> OTHER INFORMATION: e3 - hApoE (133-149)

<400> SEQUENCE: 16

Leu Arg Val Arg Leu Ala Ser His Leu Arg Lys Leu Arg Lys Arg Leu
1               5                   10                  15

Leu

<210> SEQ ID NO 17
<211> LENGTH: 20
<212> TYPE: PRT
<213> ORGANISM: Artificial Sequence
<220> FEATURE:
<223> OTHER INFORMATION: e4 - hApoE (130-149)

<400> SEQUENCE: 17
```

```
Thr Glu Glu Leu Arg Val Arg Leu Ala Ser His Leu Arg Lys Leu Arg
1               5                   10                  15

Lys Arg Leu Leu
            20

<210> SEQ ID NO 18
<211> LENGTH: 34
<212> TYPE: PRT
<213> ORGANISM: Artificial Sequence
<220> FEATURE:
<223> OTHER INFORMATION: e5 - hApoE (133-149) x 2

<400> SEQUENCE: 18

Leu Arg Val Arg Leu Ala Ser His Leu Arg Lys Leu Arg Lys Arg Leu
1               5                   10                  15

Leu Leu Arg Val Arg Leu Ala Ser His Leu Arg Lys Leu Arg Lys Arg
            20                  25                  30

Leu Leu

<210> SEQ ID NO 19
<211> LENGTH: 40
<212> TYPE: PRT
<213> ORGANISM: Artificial Sequence
<220> FEATURE:
<223> OTHER INFORMATION: e6 - hApoE (130-149) x 2

<400> SEQUENCE: 19

Thr Glu Glu Leu Arg Val Arg Leu Ala Ser His Leu Arg Lys Leu Arg
1               5                   10                  15

Lys Arg Leu Leu Thr Glu Glu Leu Arg Val Arg Leu Ala Ser His Leu
            20                  25                  30

Arg Lys Leu Arg Lys Arg Leu Leu
        35                  40

<210> SEQ ID NO 20
<211> LENGTH: 39
<212> TYPE: PRT
<213> ORGANISM: Artificial Sequence
<220> FEATURE:
<223> OTHER INFORMATION: e7 - hApoB (3371-3409)

<400> SEQUENCE: 20

Ala Leu Ser Leu Ser Asn Lys Phe Val Glu Gly Ser His Asn Ser Thr
1               5                   10                  15

Val Ser Leu Thr Thr Lys Asn Met Glu Val Ser Val Ala Thr Thr Thr
            20                  25                  30

Lys Ala Gln Ile Pro Ile Leu
        35

<210> SEQ ID NO 21
<211> LENGTH: 299
<212> TYPE: PRT
<213> ORGANISM: Artificial Sequence
<220> FEATURE:
<223> OTHER INFORMATION: apoE

<400> SEQUENCE: 21

Lys Val Glu Gln Ala Val Glu Thr Glu Pro Glu Pro Glu Leu Arg Gln
1               5                   10                  15

Gln Thr Glu Trp Gln Ser Gly Gln Arg Trp Glu Leu Ala Leu Gly Arg
            20                  25                  30

Phe Trp Asp Tyr Leu Arg Trp Val Gln Thr Leu Ser Glu Gln Val Gln
```

-continued

```
            35                  40                  45
Glu Glu Leu Leu Ser Ser Gln Val Thr Gln Glu Leu Arg Ala Leu Met
        50                  55                  60

Asp Glu Thr Met Lys Glu Leu Lys Ala Tyr Lys Ser Glu Leu Glu Glu
65                  70                  75                  80

Gln Leu Thr Pro Val Ala Glu Glu Thr Arg Ala Arg Leu Ser Lys Glu
                85                  90                  95

Leu Gln Ala Ala Gln Ala Arg Leu Gly Ala Asp Met Glu Asp Val Cys
            100                 105                 110

Gly Arg Leu Val Gln Tyr Arg Gly Glu Val Gln Ala Met Leu Gly Gln
        115                 120                 125

Ser Thr Glu Glu Leu Arg Val Arg Leu Ala Ser His Leu Arg Lys Leu
    130                 135                 140

Arg Lys Arg Leu Leu Arg Asp Ala Asp Asp Leu Gln Lys Arg Leu Ala
145                 150                 155                 160

Val Tyr Gln Ala Gly Ala Arg Glu Gly Ala Glu Arg Gly Leu Ser Ala
                165                 170                 175

Ile Arg Glu Arg Leu Gly Pro Leu Val Glu Gln Gly Arg Val Arg Ala
            180                 185                 190

Ala Thr Val Gly Ser Leu Ala Gly Gln Pro Leu Gln Glu Arg Ala Gln
        195                 200                 205

Ala Trp Gly Glu Arg Leu Arg Ala Arg Met Glu Glu Met Gly Ser Arg
    210                 215                 220

Thr Arg Asp Arg Leu Asp Glu Val Lys Glu Gln Val Ala Glu Val Arg
225                 230                 235                 240

Ala Lys Leu Glu Glu Gln Ala Gln Gln Ile Arg Leu Gln Ala Glu Ala
                245                 250                 255

Phe Gln Ala Arg Leu Lys Ser Trp Phe Glu Pro Leu Val Glu Asp Met
            260                 265                 270

Gln Arg Gln Trp Ala Gly Leu Val Glu Lys Val Gln Ala Ala Val Gly
        275                 280                 285

Thr Ser Ala Ala Pro Val Pro Ser Asp Asn His
    290                 295
```